(12) United States Patent
Maupin et al.

(10) Patent No.: US 7,629,387 B2
(45) Date of Patent: Dec. 8, 2009

(54) COMPOUNDS FOR PEST CONTROL AND METHODS FOR THEIR USE

(75) Inventors: Gary O. Maupin, Cape Coral, FL (US); Joseph Karchesy, Corvallis, OR (US); Nicholas A. Panella, Fort Collins, CO (US); Marc C. Dolan, Wellington, CO (US)

(73) Assignees: The United States of America as represented by the Secretary of the Department of Health and Human Services, Washington, DC (US); State of Oregon acting by and through the State Board of Higher Education on behalf of Oregon State University, Corvallis, OR (US)

( * ) Notice: Subject to any disclaimer, the term of this patent is extended or adjusted under 35 U.S.C. 154(b) by 443 days.

(21) Appl. No.: 11/105,807

(22) Filed: Apr. 13, 2005

(65) Prior Publication Data

US 2005/0176818 A1     Aug. 11, 2005

Related U.S. Application Data

(63) Continuation of application No. 10/450,024, filed as application No. PCT/US01/47736 on Dec. 7, 2001, now Pat. No. 7,129,271.

(60) Provisional application No. 60/254,311, filed on Dec. 8, 2000.

(51) Int. Cl.
*A61K 31/12* (2006.01)
*A01N 25/00* (2006.01)

(52) U.S. Cl. .................... 514/691; 424/405

(58) Field of Classification Search ............... None
See application file for complete search history.

(56) References Cited

U.S. PATENT DOCUMENTS

| | | | |
|---|---|---|---|
| 3,880,931 A | | 4/1975 | Bozzato et al. |
| 3,966,959 A | * | 6/1976 | Addor .................. 514/531 |
| 4,195,080 A | | 3/1980 | Herrera et al. |
| 4,497,838 A | | 2/1985 | Bonnell |
| 4,904,645 A | | 2/1990 | Puritch et al. |
| 4,973,485 A | * | 11/1990 | Rich .................. 426/534 |
| 5,576,011 A | | 11/1996 | Butler et al. |
| 5,847,226 A | | 12/1998 | Muller et al. |
| 5,858,738 A | | 1/1999 | Lingham et al. |
| 6,074,634 A | | 6/2000 | Lopez, Jr. et al. |
| 6,114,384 A | | 9/2000 | Bessette et al. |
| 2004/0005343 A1 | | 1/2004 | Zhu et al. |
| 2004/0157935 A1 | | 8/2004 | Henderson et al. |

FOREIGN PATENT DOCUMENTS

| | | | |
|---|---|---|---|
| EP | 10033076 A1 | * | 9/2000 |
| EP | 1033076 | | 12/2000 |
| JP | 55045649 | | 3/1980 |
| JP | 10087409 | | 4/1998 |
| JP | 11240802 | | 9/1999 |
| WO | WO 95/17816 | | 7/1995 |
| WO | WO 99/05910 | | 2/1999 |
| WO | WO 99/25196 A1 | * | 5/1999 |
| WO | WO 00/27197 | | 5/2000 |
| WO | WO 00/27907 | | 5/2000 |
| WO | WO 01/28343 | | 4/2001 |

OTHER PUBLICATIONS

Bombarda, "Sesquiterpenic Epoxides and Alcohols Derived from Hydrocarbons of Vetiver Essential Oil," *J. Agic. Food Chem.*, 44(1):217-222, 1996.
CAS Registry No. 5090-66-4.
CAS Registry No. 103425-24-7.
Cas Registry No. 141695-90-1.
Castillo et al., "Biological Activities of Natural Sesquiterpene Lactones and the Effect of Synthetic Sesquiterpene Derivatives on Insect Juvenile Hormone Biosynthesis," *J. Agric. Food Chem.*, vol. 46, pp. 2030-2035 (1998).
Maupin et al., "Acaricide Susceptibility of Immature *Ixodes scapularis* (Acari:Ixodidae) as Determined by the Disposable Pipet Method," *Journal of Medical Entomology*, vol. 31, No. 2, 3 pp., Mar. 1994.
McDaniel, "Major termiticidal components of heartwood of Port-Oxford-cedar, *Chamaecyparis lawsoniana* (A. Murr.) Parl.," *Material und Organismen* 24(1):1-15, 1989.
Miyazawa et al., "Insecticidal Sesquiterpene from *Alpinia oxyphylla* against *Drosophila melanogaster*," I Agric. Food Chem., vol. 48, pp. 3639-3641 (2000).
Panella et al., "Susceptibility of Immature *Ixodes scapularis* (Acari: Ixodidae) to Plant-Derived Acaricides," *Journal of Medical Entomology*, 34(3):340-345, May 1997.
Smadja, "Review on Chemical Composition of Vetiver Oil," *J. Nature* 3(1):3-17, 1991.
Tellez et al., "Composition and Some Biological Activities of the Essential Oil of *Callicarpa Americana* (L.)," *J. Agric. Food Chem.*, vol. 48, pp. 3008-3012 (2000).
*The Vetiver Newsletter*, No. 22, Nov. 2000, 43 pages.

* cited by examiner

*Primary Examiner*—Paul A Zucker
(74) *Attorney, Agent, or Firm*—Klarquist Sparkman, LLP

(57) ABSTRACT

Compounds, compositions, and methods for controlling an arthropod pest population that employ an eremophilane sesquiterpene parent structure are presented. The compounds have minimal adverse or toxic effects on humans, non-human animals, and the natural environment. The compounds may be isolated from natural sources, semi-synthesized from naturally occurring compounds, or completely synthesized. The compounds may be applied directly to a pest, or the locus of a pest, and function as topical or ingestible toxins. Eremophilane sesquiterpenes 13-hydroxy-valencene, valencene-11, 12-epoxide, valencene-13-aldehyde, and nootkatone-1,10-11,12-diepoxide are exemplary compounds.

27 Claims, 2 Drawing Sheets

COMPOUNDS FOR PEST CONTROL AND METHODS FOR THEIR USE

CROSS REFERENCE TO RELATED APPLICATIONS

This application is a continuation of U.S. patent application Ser. No. 10/450,024, filed Nov. 10, 2003, now U.S. Pat. No. 7,129,271, which is a U.S. national stage application under 35 U.S.C. §371 of International Application No. PCT/US01/47736, filed Dec. 7, 2001, which claims the benefit of U.S. Provisional Patent Application No. 60/254,311, filed Dec. 8, 2000, each of which applications is herein incorporated by reference in its entirety.

FIELD

This invention relates to compositions for controlling pest populations and methods for their use. In addition, this invention relates to pesticidal compositions for controlling arthropod pests.

BACKGROUND

Pests such as insects, arachnids, and acarines are detrimental to humans. Pests include pathogenic organisms that infest mammals and plants, such as those that infest or feed upon plants and livestock, thus causing economic loss or diminishment of plant crops, plant products, and livestock. For example, the glassy-winged sharpshooter is a pest that feeds on grape vines, thus diminishing the crop available for wine production. Other pests may infest structures such as dwellings, residences, hospitals, and commercial establishments, such as restaurants and retail stores. These pests may be detrimental to the structure, such as termites feeding on wooden beams, or simply be a nuisance to people who visit or live in infested buildings. Additionally, some pests are vectors for certain diseases that harm humans and non-human animals, including pets and livestock.

The transmission of vector-born diseases through pests is a problem throughout the world and is best controlled through the control of those vectors. For example, the deer tick (*Ixodes scapularis*) may transmit Lyme disease to a host when feeding on the host's blood by passing an infectious microbe (*Borrelia burgdorferi*), which lives in the tick's gut, into the host's bloodstream. A mosquito (*Aedes aegypti*), prevalent throughout many tropical and sub-tropical regions of the world, may transmit Dengue Fever, Yellow Fever, or encephalitis viruses to a host on which it feeds. The rat flea (*Xenopsylla cheopis*) is a vector for the microbe (*Yersinia pestis*) that causes the Plague.

Pest control is often difficult to achieve. Many pesticides are toxic to humans and animals and may pollute the environment. Hence, a number of commonly used pesticides, such as organophosphates, have been restricted or made commercially unavailable. Biopesticides derived from natural sources, such as plants, fungi, or other natural products, offer a safer alternative to chemically synthesized pesticides. Biopesticides generally have fewer health effects and can be better for the environment, but many biopesticides offer substantially weaker control of pests, or control only a limited spectrum of pests, while other biopesticides may be environmentally toxic. For example, pyrethrins—pesticides made from the extract of the chyrsanthemum plant—control a wide variety of pests, but are very toxic to fish, such as bluegill and lake trout. Additionally, pests may become resistant to certain compounds after continued use; for example, insect resistance to pyrethrins already has been observed. Thus, new pest control agents offer an alternative for commonly used pesticides.

Therefore, a need exists for an effective pesticide capable of controlling a variety of pests, for example vectors of disease, that is relatively safe for humans, animals, plants, and the environment.

SUMMARY

Compounds, compositions, and methods for controlling arthropods are disclosed. The compounds are based on an eremophilane sesquiterpene parent structure and, when used as pesticides or pest control agents, have minimal adverse or toxic effects on humans, non-human animals, and the natural environment. The compounds are effective against arthropods, such as insects and acarines, including (but not limited to) members of the taxonomic order or subclass Acarina, Diptera, Homoptera, or Siphonoptera.

Certain exemplary pesticidal eremophilane sesquiterpenes described in this specification are represented by Formulas I, II, III, IV, V and/or VI, as discussed below, and may be isolated from natural sources, such as Alaska yellow Cedar, *Alpinia* species, bitter cardamom, and citrus fruits. Additionally, valencene, nootkatol, epinootkatol, nootkatone, and nootkatene may be used as starting materials to synthesize some of the described compounds. Thus, the compounds are understood to be biocides and/or biorational. Particular examples of such pesticidal eremophilane sesquiterpenes are β-hydroxy-valencene, valencene-11,12-epoxide, valencene-13-aldehyde, and nootkatone-1,10-11,12-diepoxide.

Articles of manufacture also are disclosed. In some embodiments, the article of manufacture includes a vessel containing a pesticidal compound, such as a bottle, tube, or can. In other embodiments, the article of manufacture includes a device comprising the compound, such as a flea collar, pest control strip, or rodent trap.

Some embodiments employ a method of controlling an arthropod. In such embodiments, an arthropod is contacted with a pesticidally effective amount of a compound described herein sufficient to cause an adverse effect on the arthropod. In specific embodiments, the arthropod is killed or repelled from a locus, though other adverse effects leading to pest control, such as inducing sterility or inhibiting oviposition, are possible.

All compounds described herein may be used in pure form or in the form of a pesticidally acceptable salt or pesticidal composition. The compounds may function as pest repellents as well as pesticides, and certain compounds have a lethal effect on certain arthropods. The compounds may be applied directly to a pest, or the locus of a pest, and function as topical or ingestible toxins. The compounds may be used to kill pests on, or repel pests from, humans, non-human animals, and plants, including household, industrial, recreational, veterinary, agricultural, silvicultural, horticultural, and environmental uses. Additionally, the compounds may be used to control the spread of disease by controlling the arthropod vector for that disease, such as killing the vector to inhibit transmission of the disease to the host.

BRIEF DESCRIPTION OF THE DRAWINGS

FIG. 1A illustrates the separation of seven fractions (I-VII) by a chromatographic process using hexane/diethyl ether as a solvent, and FIG. 1B illustrates the separation of three fractions by a chromatographic process using $CH_2Cl_2$/diethyl ether.

DETAILED DESCRIPTION

Figure 1A:
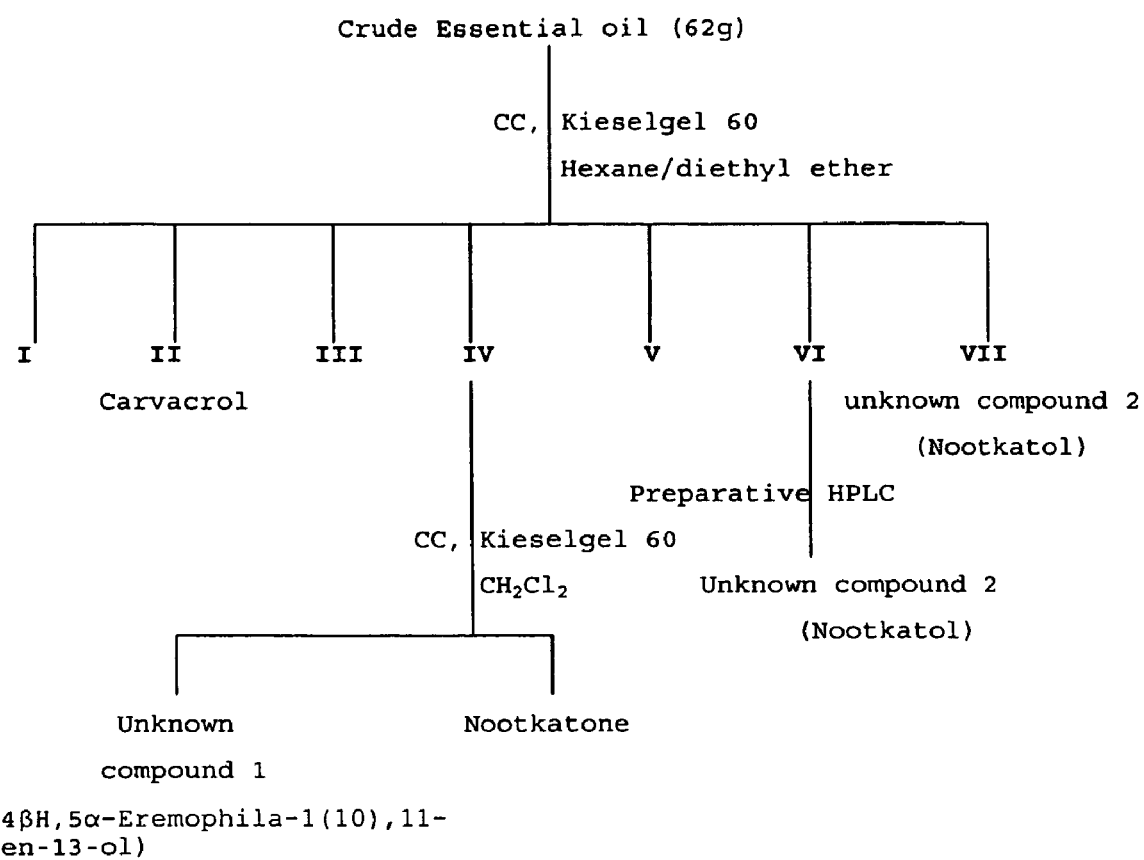
FIGS. 1A and 1B illustrate one method of separating the components of heartwood essential oil.

Compounds, compositions, and methods for controlling an arthropod pest population are provided; The compounds used comprise an eremophilane sesquiterpene and are believed to be substantially nontoxic to both plants and animals. The pest population may be, for example, a pathogenic organism population that feeds upon, damages, irritates, or otherwise adversely affects an animal or plant host. In particular embodiments, the pest functions as a vector for disease. When used as pesticides or pest control agents, these compounds have minimal adverse effects on humans, domesticated animals, wildlife, and/or the natural environment.

Explanations of Terms

Unless otherwise noted, technical terms are used according to conventional usage. In order to facilitate review of the various embodiments of the invention, the following explanations of terms are provided:

As used herein, the singular forms "a," "an," and "the," refer to both the singular as well as plural, unless the context clearly indicates otherwise. For example, the term "a pesticidal compound" includes single or plural pesticidal compounds and can be considered equivalent to the phrase "at least one pesticidal compound."

As used herein, the term "comprises" means "includes." For example, "comprising A or B" means "includes A," "includes B," or "includes both A and B."

The term "alcohol" refers to an aliphatic containing one or more hydroxyl groups, including (but not limited to) ethanol, methanol, or propanol. A "lower aliphatic alcohol" is an alkane, alkene, or alkyne of one to six carbon atoms substituted with a hydroxyl group.

The term "aliphatic" refers to straight or branched chain alkanes, alkenes, and alkynes. The term "lower aliphatic" refers to straight or branched chain alkanes, alkenes, and alkynes of 1 to 10 carbons, for example 1 to 6 carbon atoms. An aliphatic may be unsubstituted or substituted, for example, with an —OH group to form a lower aliphatic alcohol.

The term "alkenyl" refers to a straight or branched chain alkyl radical containing at least two carbon atoms and having one carbon-carbon double bond. The term "lower alkenyl" refers to an alkenyl containing from two to six carbon atoms, including (but not limited to): vinyl, 2-propenyl, 2-methyl-2-propenyl, 3-butenyl, 4-pentenyl, and 5-hexenyl.

The term "alkoxy" refers to a substituted or unsubstituted alkoxy, where an alkoxy has the structure —O—R, where R is a substituted or unsubstituted alkyl. In an unsubstituted alkoxy, the R is an unsubstituted alkyl. The term "substituted alkoxy" refers to a group having the structure —O—R, where R is alkyl substituted with a non-interfering substituent. "Lower alkoxy" refers to any alkoxy in which R is a lower alkyl. "Thioalkoxy" refers to —S—R, where R is substituted or unsubstituted alkyl.

The term "alkoxyalkyl" refers to an alkoxy group appended to a lower alkyl radical.

The term "alkyl" refers to a cyclic, branched, or straight chain alkyl group which, unless otherwise described, contains one to twelve carbon atoms. This term is exemplified by groups such as (but not limited to) methyl, ethyl, n-propyl, isobutyl, t-butyl, pentyl, pivalyl, heptyl, adamantyl, and cyclopentyl. Alkyl groups can be unsubstituted or substituted with one or more substituents, for example halogen, alkyl, alkoxy, alkylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality. The term "lower alkyl" refers to a cyclic, branched or straight chain alkyl of one to six carbon atoms. This term is further exemplified by such groups as methyl, ethyl, n-propyl, i-propyl, n-butyl, t-butyl, i-butyl (or 2-methylpropyl), sec-butyl, n-pentyl, cyclopropylmethyl, i-amyl, n-amyl, n-pentyl, 1-methylbutyl, 2,2-dimethylbutyl, 2-methylpentyl, 2,2-dimethylpropyl, n-hexyl. Lower alkyl groups can be unsubstituted or substituted. One specific example of a substituted alkyl is 1,1-dimethyl propyl.

The term "alkylamino" refers to an alkyl group where at least one hydrogen is substituted with an amino group.

The term "amino" refers to a chemical functionality —$NR_1R_2$ where $R_1$ and $R_2$ are independently hydrogen, alkyl, or aryl.

An "analog" is a molecule that differs in chemical structure from a parent compound. Examples include, but are not limited to: a homolog (which differs by an increment in the chemical structure, such as a difference in the length of an alkyl chain); a molecular fragment; a structure that differs by one or more functional groups; or a structure that differs by a change in ionization, such as a radical. Structural analogs are often found using quantitative structure activity relationships (QSAR), with techniques such as those disclosed in *Remington: The Science and Practice of Pharmacology*, 19$^{th}$ Edition (1995), chapter 28. A derivative is a biologically active molecule derived from the base molecular structure. A mimetic is a biomolecule that mimics the activity of another biologically active molecule. Biologically active molecules can include chemical compounds that mimic the pesticidal activities of the compounds disclosed herein.

An "animal" is a living multicellular vertebrate organism, a category which includes, for example, mammals, reptiles, arthropods, and birds.

The term "aryl" refers to a monovalent unsaturated aromatic carbocyclic group having a single ring (e.g., phenyl, benzyl) or multiple condensed rings (e.g., naphthyl or anthryl), which can be unsubstituted or substituted with, for example, halogen, alkyl, alkoxy, mercapto (—SH), alkylthio, trifluoromethyl, acyloxy, hydroxy, carboxy, aryloxy, aryl, arylalkyl, heteroaryl, amino, alkylamino, dialkylamino, morpholino, piperidino, pyrrolidin-1-yl, piperazin-1-yl, or other functionality.

Some compounds described herein are pesticides of biological origin obtained from a naturally occurring substance or organism. Such substances are commonly called "biocides." Certain compounds are understood to be "biorational," because the compound is a chemical substance of natural origin that can be synthesized. Pesticides having an active ingredient selected from compounds according to any of Formulas I-V that are biorational chemicals qualify for the United States Environmental Protection Agency's Biorational Program.

"=C" refers to a double-bonded carbon atom.

"Carbonyl-containing" refers to any substituent containing a carbon-oxygen double bond (C=O), including substituents based on —COR or —RCHO where R is an aliphatic or lower aliphatic (such as alkyl or lower alkyl), hydroxyl, or a secondary, tertiary, or quaternary amine. Carbonyl-containing groups include, for example, aldehydes, ketones, carboxylic acids, and esters. Alternatively, "carbonyl-containing group" refers to —$R_1COR_2$ groups wherein $R_1$ and $R_2$ are independently aliphatic, lower aliphatic (such as alkyl or lower alkyl), hydroxyl, or secondary, tertiary, or quaternary amine.

Examples include —COOH, CH$_2$COOH, —CH$_2$COOCH$_3$, —CH$_2$CONH$_2$, —CH$_2$CON(CH$_3$)$_2$.

"Carboxyl" refers to the radical —COOH, and substituted carboxyl refers to —COR where R is alkyl, lower alkyl, or a carboxylic acid or ester.

"Conjugate" refers to an acid and a base that can convert to each other by the gain or loss of a proton.

The term "dialkylamino" refers to —N—R—R' wherein R and R' are independently selected from lower alkyl groups.

The term "dialkylaminoalkyl" refers to —N—R—R', which is appended to a lower alkyl radical, wherein R and R' are independently selected from lower alkyl groups.

The term "halogen" refers to the elements fluourine, bromine, chlorine, and iodine, and the term "halo" refers to fluoro, bromo, chloro and iodo substituents.

The term "heterocycle" (or "heterocyclic") refers to a monovalent saturated, unsaturated, or aromatic carbocyclic group having a single ring (e.g., benzyl, morpholino, pyridyl or furyl), or multiple condensed rings (e.g., naphthyl, quinolinyl, indolizinyl or benzo[b]thienyl). Additionally, some heterocyles may contain a heteroatom, (such as as N, O, P, or S) in place of a carbon atom within the ring structure. A heterocycle can be unsubstituted or substituted with, for example, halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality. Examples include, but are not limited to, aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl, and pyrazinyl.

The term "(heterocyclic)alkyl" as used herein refers to a heterocyclic group appended to a lower alkyl radical including, but not limited to, pyrrolidinylmethyl and morpholinylmethyl.

The term "host" includes animal, plant, and fungal hosts.

"Hydroxyl" refers to —OH.

"Hydroxyalkyl" refers to —R—OH, wherein R is alkylene, especially lower alkylene (for example in methylene, ethylene, or propylene). A hydroxyalkyl group may be either linear or branched, such as 1-hydroxyisopropyl.

The term "mammal" includes both human and non-human mammals.

The term "=O" indicates a double-bonded oxygen moiety.

"Oxygen-containing group" refers to an R-group containing at least one oxygen atom. Exemplary, non-limiting oxygen containing groups include oxygen alone (which may be attached to the molecule by a single or double bond), hydroxyl, hydroxylalkyl, or any group containing a carbonyl moiety.

As used herein, the terms "pest," "pest organism" and "pest population" refer to arthropods, including pathogens and parasites, that negatively affect host plants or animals, including humans, by colonizing, attacking, irritating, or feeding upon them, or competing for host nutrients. The terms "parasite" and "parasitic" refer to all arthropod endoparasites and ectoparasites of hosts. Some pests function as disease vectors capable of spreading disease to a host population.

Exemplary arthropods include, without limitation, the following arthropods described according to taxonomic designation and/or vernacular name:

Order Acarina, including *Acarus siro, Aceria sheldoni, Aculus schlechtendali, Amblyomma* species, *Argas* species, *Boophilus* species, *Brevipalpus* species, *Bryobia praetiosa, Calipitrimerus* species, *Chorioptes* species, *Dermanyssus gallinae, Eotetranychus carpini, Eriophyes* species, *Hyalomma* species, *Ixodes* species, *Olygonychus pratensis, Ornithodoros* species, *Panonychus* species, *Phyllocoptrum oleivora, Polyphagotarsonemus latus, Psoroptes* species, *Rhipicephalus* species, *Rhizoglyphus* species, *Sarcoptes* species, *Tarsonemus* species, and *Tetranychus* species, *Dermacentor* species.

Order Homoptera, including *Aleurothrixus floccosus, Aleyrodes brassicae, Aonidiella* species, *Aphididae* species, *Aphis* species, *Aspidiotus* species, *Bemisia tabaci, Ceroplaster* species, *Chrysomphalus aonidium, Chrysomphalus dictyospermi, Coccus hesperidum, Empoasca* species, *Eriosoma lanigerum, Erythroneura* spp, *Gascardia* species, *Laodelphax* species, *Lecanium corni, Lepidosaphes* species, *Macrosiphus* species, *Myzus* species, *Nephotettix* species, *Nilaparvata* species, *Paratoria* species, *Pemphigus* species, *Planococcus* species, *Pseudaulacaspis* species, *Pseudococcus* species, *Psylia* species, *Pulvinaria aethiopica, Quadraspidiotus* species, *Rhopalosiphum* species, *Saissetia* species, *Scaphoideus* species, *Schizaphis* species, *Sitobion* species, *Trialeurodes vaporariorum, Trioza erytreae, Unaspis citri*; and *Homalodisca coagulata;*

Order Hymenoptera, including Family Formicidae, Family Apidae, and Family Bombidae, such as *Acromyrmex* species, *Atta* species, *Cephus* species, *Diprion* species, *Diprionidae* species, *Gilpinia polytoma, Hoplocampa* species, *Lasius* species, *Monomorium pharaonis, Neodiprion* species, *Solenopsis* species, and *Vespa* species;

Order Diptera, including Family Culicidae, Family Simulidae, Family Psychodidae, Family Ceratopogonidae, Family Sarcophagidae, Family Streblidae, and Family Nycteribiidae, such as *Aedes* species, *Antherigona soccata, Bibio hortulanus, Calliphora erythrocephala, Ceratitis* species, *Chrysomyia* species, *Culex* species, *Culex p. pipiens, Cuterebra* species, *Dacus* species, *Drosophila* species, *Fannia* species, *Gastrophilus* species, *Glossina* species, *Hypoderma* species, *Hyppobosca* species, *Liriomyza* species, *Lucilia* species, *Melanagromyza* species, *Musca* species, *Oestrus* species, *Orseolia* species, *Oscinella frit, Pegomyia hyoscyami, Phorbia* species, *Rhagoletis pomonella, Sciara* species, *Stomoxys* species, *Tabanus* species, *Tannia* species, and *Tipula* species;

Order Siphonaptera, including *Ceratophyllus* species, *Xenopsylla cheopis, Ctenocephalides* species, *Oropsylla* species, *Tulex* species and *Diamanus* species.

Order Thysanura, including *Lepisma saccharina;*

Order Lepidoptera; including *Acleris* species, *Adoxophyes* species, *Aegeria* species, *Agrotis* species, *Alabama argulaceae, Amylois* species, *Anticarsia gemmatalis, Archips* species, *Argyrotaenia* species, *Autographa* species, *Busseola fusca, Cadra cautella, Carposina nipponensis, Chilo* species, *Choristoneura* species, *Clysia ambigueua, Cnaphalocrocis* species, *Cnephasia* species, *Cochylis* species, *Coleophora* species, *Crocidolomia binotaus, Cryptophlebia leucotreta, Cydia* species, *Diatraea* species, *Diparopsis castanea, Earias* species, *Ephestia* species, *Eucosma* species, *Eupoecilia ambiguena, Euproctis* species, *Euxoa* species, *Grapholita* species, *Hedya nubiferana, Heliothis* species, *Hellula andalis, Hyphantria cunea, Keiferia lycopersicella, Leucoptera scitella, Lithocllethis* species, *Lobesia botrana, Lymantria* species, *Lyonetia* species, *Malacosoma* species, *Mamestra brassicae, Manduca sexta, Operophtera* species, *Ostrinia nubilalis, Pammene* species, *Pandemis* species, *Panolis flammea, Pectinophora gossypieua, Phthorimaea operculeua, Pieris rapae, Pieris* species, *Plutella xylostella, Prays* species, *Scirpophaga* species, *Sesamia* species, *Sparganothis* species, *Spodoptera* species, *Synanthedon* species, *Thaumetopoea* species, *Tortrix* species, *Trichoplusia ni,* and *Yponomeuta* species;

Order Coleoptera, including *Agriotes* species, *Anthonomus* species, *Atomaria linearis, Chaetocnema tibialis, Cosmopolites* species, *Curculio* species, *Dermestes* species, *Diabrotica* species, *Epilachna* species, *Eremnus* species, *Leptinotarsa decemlineata, Lissorhoptrus* species, *Melolontha* species, *Oryzaephilus* species, *Otiorhynchus* species, *Phlyctinus* species, *Popillia* species, *Psylliodes* species, *Rhizopertha* species, *Scarabeidae, Sitophilus* species, *Sitotroga* species, *Tenebrio* species, *Tribolium* species, and *Trogoderma* species;

Order Orthoptera, including *Blatta* species, *Blattella* species, *Gryllotalpa* species, *Leucophaea maderae, Locusta* species, *Periplaneta* species, and *Schistocerca* species Order Isoptera, including *Reticulitermes* species;

Order Psocoptera, including *Liposcelis* species;

Order Anoplura, including *Haematopinus* species, *Phthirus pubis; Linognathus* species, *Pediculus* species, *Pemphigus* species, and *Phylloxera* species;

Order Mallophaga, including *Damalinea* species and *Trichodectes* species;

Order Thysanoptera, including *Frankliniella* species, *Hercinothrips* species, *Taeniothrips* species, *Thrips palmi, Thrips tabaci* and *Scirtothrips aurantii* and Order Heteroptera, including *Cimex* species, *Distantiella theobroma, Dysdercus* species, *Euchistus* species, *Eurygaster* species, *Leptocorisa* species, *Nezara* species, *Piesma* species, *Rhodnius* species, *Sahlbergella singularis, Scotinophara* species and *Triatoma* species.

Order Scopriones, including *Centruriodes* species, *Euscorpius* species, *Parabuthus* species, and *Vaejovis* species.

Order Araneae, including *Latrodectus* species, *Loxosceles* species, and *Brachypelma* species.

Order Hemiptera, including *Cimicidae* species, *Enicocephalidae* species, *Pentatomidae* species, *Gerridae* species, *Saldidae* species, *Belostomatidae* species, and *Nepidae* species.

Class Diplipoda (millipedes).

Class Chilopoda (centipedes).

In particular embodiments, the pest is a member of the taxonomic order or subclass Acarina, including soft and hard ticks; Diptera, including Tabanidae, anophelines, and culecines; or Siphonoptera. In other particular embodiments, the pest belongs to a particular species, such as *Ixodes scapularis* (deer tick), *Aedes aegypti* (mosquito), *Xenopsylla cheopis* (rat flea), *Homalodisca coagulata* (glassy-winged sharpshooter), or *Culex pithiens* (mosquito).

Other exemplary arthropod pests and/or parasites include fleas; mosquitoes; bees, yellow jackets, and wasps; cockroaches, including the American and German cockroach; termites; houseflies and silverleaf whiteflies; lacey-winged sharpshooters or glassy-winged sharpshooters; leaf hoppers, such as the grape or potato leafhoppers; cabbage looper (Lepidoptera); ants, such as the pharaoh ant, argentine ant, carpenter ant, and fire ant; stink or lygus bugs; leafminers; western flower thrips; aphids, such as melon aphids and black bean aphids; arachnids, such as spiders, ticks, and plant mites, including two-spotted spider mites, McDaniel mites, Pacific mites, and European mites.

A "pest control agent" is a compound or composition that controls the behavior of a pest by causing an adverse effect on that pest, including (but not limited to) physiological damage to the pest; inhibition or modulation of pest growth; inhibition or modulation of pest reproduction; inhibition or complete deterrence of pest movement into a locus; initiation or promotion of pest movement away from a locus; inhibition or complete suppression of pest feeding activity; or death of the pest. A pest control agent may be considered a "pesticide" if it kills at least one individual in a pest population. Additionally, a pest control agent may be non-lethal at a particular concentration or amount (such as a deterrent of pests) and a pesticide at a different concentration or amount. A "pesticidally effective amount" of a compound refers to an amount that has an adverse biological effect on at least some of the pests exposed to the pesticide or pest control agent. For example, the effective amount of a compound may be an amount sufficient to repel a pest from a locus, induce sterility in a pest, or inhibit oviposition in a pest. As another example, a "pesticidally effective amount" of a compound is capable of killing at least some individuals in a pest population. In specific embodiments, this pesticide is fatal to at least 10% of the pests treated. In particular embodiments, the pesticidally effective amount kills at least 20%, or even 50%, of the pest population. In more particular embodiments, the pesticidally effective amount kills over 90%, and nearly 100%, of the pest population. Specific examples of pesticidally effective amounts and treatments are provided in the Examples below. The term "amount sufficient to inhibit infestation" refers to that amount sufficient to deter, depress, or repel a portion of a pest population so that a disease or infected state in a host population is inhibited or avoided.

A pesticidally effective amount, or an amount sufficient to inhibit infestation, for a given compound may be determined by routine screening procedures employed to evaluate pesticidal activity and efficacy. Some such routine screening procedures are discussed in the Examples below or in Maupin, G. O., and Piesman, J., J. Med. Entomol., 31: 319-21 (1994). Particular examples of pesticidal compounds described herein have an $LD_{50}$ or $LC_{50}$ of about $65 \times 10^{-3}$ or less, such as less than $25 \times 10^{-3}$, less than $10 \times 10^{-3}$, less than $5 \times 10^{-3}$, less than $5 \times 10^{-3}$, than $3 \times 10^{-3}$, or even less than $1 \times 10^{-3}$.

Compounds or compositions having a higher level of pesticidal activity can be used in smaller amounts and concentrations, while compounds or compositions having a lower level of pesticidal activity may require larger amounts or concentrations in order to achieve the same pestical effect. Additionally, some compounds or compositions demonstrating pesticidal activity may demonstrate non-lethal pest control effects at a different concentration or amount, such as a lower concentration or amount. Non-lethal pest control effects include anti-feeding, reduced fecundity, reduced oviposition, inhibited ecdysis, and sterility.

The term "phenyl" refers to a phenyl group, which may be unsubstituted or substituted, for example, with a substituent selected from lower alkyl, alkoxy, thioalkoxy, hydroxy and halo.

The term "phenylalkyl" refers to a phenyl group appended to a lower alkyl radical including, but not limited to, benzyl, 4-hydroxybenzyl, 4-chlorobenzyl, and 1-naphthylmethyl.

The term "subject" includes both human and veterinary subjects, such as primates, canines, felines, and rodents.

The term "thioalkoxyalkyl" refers to a thioalkoxy group appended to a lower alkyl radical.

Other chemistry terms herein are used according to conventional usage in the art, as exemplified by *The McGraw-Hill Dictionary of Chemical Terms* (1985) and *The Condensed Chemical Dictionary* (1981).

All chemical compounds include both the L- and D-stereoisomers, as well as either the L- or D-stereoisomer, unless otherwise specified.

Compounds and Compositions

The compounds described herein are terpenes and terpene derivatives, including sesquiterpenes and sesquiterpene derivatives based on a root structure having the formula $C_{15}H_{24}$, though analogs of sesquiterpenes and sesquiterpene derivatives may be produced by additions and substitutions of chemical moities. In particular embodiments, the compounds comprise eremophilane sesquiterpenes, natural product two-ring sesquiterpenes based on eremophilane as a parent structure:

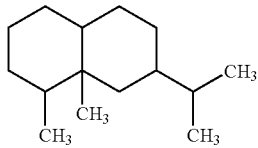

Eremophilane and eremophilane sesquiterpenes are further described in W. M. B. Konst, et al., *Flavours* (March/April 1975), pages 121-125; and International Union of Pure and Applied Chemistry, *Nomenclature of Organic Chemistry: Section F-Natural Products and Related Compounds, Recommendations* 1976, IUPAC Information Bulletin Appendices on Tentative Nomenclature, Symbols, Units, and Standards, No. 53, December, 1976 (also found in: *Eur. J. Biochem.* 86: 1-8 (1978)).

The pesticidal eremophilane sesquiterpenes described herein may be represented by Formula I:

Formula I

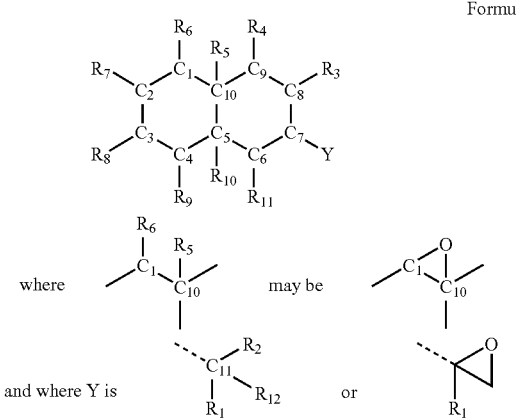

and $R_1$, $R_2$, $R_3$, $R_4$, $R_5$, $R_6$, $R_7$, $R_8$, $R_9$, $R_{10}$, $R_{11}$, and $R_{12}$ are each independently selected from H, $=O$, $-OH$, lower aliphatic, lower aliphatic alcohol, lower aliphatic thiol, carbonyl containing lower aliphatic, thiocarbonyl containing lower aliphatic, lower aliphatic ether, or lower aliphatic epoxide. Additionally, the selection of $R_1$, $R_2$, $R_3$, $R_4$, $R_5$, $R_6$, $R_7$, $R_8$, $R_9$, $R_{10}$, $R_{11}$, and $R_{12}$ should satisfy valence requirements.

In some embodiments, one or two of the bonds $C_1$-$C_2$, $C_2$-$C_3$, $C_3$-$C_4$, $C_4$-$C_5$, $C_5$-$C_{10}$, $C_5$-$C_6$, $C_6$-$C_7$, $C_7$-$C_8$, $C_8$-$C_9$, $C_9$-$C_{10}$, or $C_{10}$-$C_1$ is a double bond. If $C_{10}$-$C_1$ or $C_9$-$C_{10}$ is a double bond, then $R_5$ is absent to satisfy valence requirements. In some embodiments, one or two ring bonds in the left ring (i.e., $C_1$-$C_2$, $C_2$-$C_3$, $C_3$-$C_4$, $C_4$-$C_5$, $C_5$-$C_{10}$, or $C_{10}$-$C_1$) is a double bond, or one or two of the ring bonds in the right ring (i.e., one of the bonds $C_5$-$C_{10}$, $C_5$-$C_6$, $C_6$-$C_7$, $C_7$-$C_8$, $C_8$-$C_9$, or $C_9$-$C_{10}$) is a double bond, or one of the ring bonds in each ring is a double bond. In particular embodiments, a double bond is located at a particular position on the ring structure, such as a double bond at either $C_1$-$C_{10}$ or $C_8$-$C_9$ or both $C_1$-$C_{10}$ or $C_8$-$C_9$. Additionally, any of $C_1$-$C_{10}$ may be carbon, CH, or $CH_2$, as appropriate, to satisfy valence requirements. In particular embodiments, $C_{10}$-$C_1$ is a double bond, and in more particular embodiments, both $C_1$-$C_{10}$ and $C_8$-$C_9$ are double bonds.

In some embodiments, a compound according to Formula I is a specific stereoisomer, such as:

Formula I

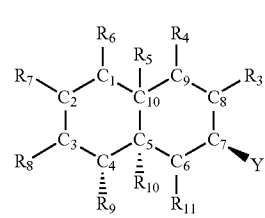

In some embodiments, lower aliphatic is a lower alkyl, lower aliphatic alcohol is a lower alkyl alcohol, lower aliphatic thiol is an alkyl thiol, carbonyl containing lower aliphatic is a carbonyl containing lower alkyl, thiocarbonyl containing lower aliphatic is a thiocarbonyl containing lower alkyl, lower aliphatic ether is a lower alkyl ether, and lower aliphatic epoxide is a lower alkyl epoxide.

In some embodiments, one or more of the R-groups on the ring structure ($R_3$-$R_{11}$) are H while the remainder are certain substituents, such as $=O$, $-OH$, lower aliphatic alcohol, carbonyl containing lower aliphatic, lower aliphatic ether, or lower aliphatic epoxide. For example, all of $R_3$-$R_{11}$ may be H, or all but two or three of $R_3$-$R_{11}$ may be H. In particular embodiments, $R_3$, $R_4$, $R_5$ $R_6$, $R_8$, and $R_{11}$ are H and $R_7$, $R_9$, and $R_{10}$ are other R-groups, such as $=O$, $-OH$, lower alkyl alcohol, lower alkyl thiol, carbonyl containing lower alkyl, thiocarbonyl containing lower alkyl, lower alkyl ether, or lower alkyl epoxide. In more particular embodiments, $R_9$, and $R_{10}$ are lower alkyl, such as methyl. In other particular embodiments, $R_7$ is an oxygen-containing group, such as $=O$, $-OH$, lower aliphatic alcohol, lower alkyl epoxide, or carbonyl containing lower aliphatic.

In some embodiments, Y is

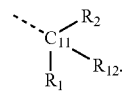

In particular embodiments, one of the bonds $C_{11}$-$R_1$ or $C_1$-$R_2$ is a double bond and $R_{12}$ is absent. In more particular embodiments, the $C_{11}$-$R_2$ bond is a double bond.

In some embodiments, $R_1$, $R_2$, and $R_{12}$ are independently H, $=O$, $-OH$, lower aliphatic (for example, lower alkyl), lower aliphatic alcohol (for example, lower alkyl alcohol), lower aliphatic ether (for example, lower alkyl ether), carbonyl-containing lower aliphatic (for example, carbonyl-containing alkyl), or lower aliphatic epoxide (for example, lower alkyl epoxide). In particular embodiments, $R_2$ is $=O$, with the bond $C_{11}$-$R_2$ being a double bond. In even more particular embodiments, $R_1$ is lower aliphatic alcohol, such as a lower alkyl alcohol (e.g., $-CH_2OH$), or lower aliphatic, such as lower alkyl (e.g., methyl or ethyl).

In some embodiments, Y is

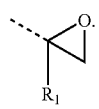

In particular embodiments, $R_1$ is H, —OH, lower aliphatic (for example, lower alkyl), lower aliphatic alcohol (for example, lower alkyl alcohol), carbonyl-containing lower aliphatic, lower aliphatic ether (for example, lower alkyl ether) or lower aliphatic epoxide (for example, lower alkyl epoxide). In even more particular embodiments, $R_1$ is lower aliphatic alcohol, such as lower alkyl alcohol (e.g., —CH$_2$OH) or lower aliphatic, such as lower aklyl (e.g., methyl or ethyl).

Certain exemplary pesticidal eremophilane sesquiterpenes are represented by Formula II:

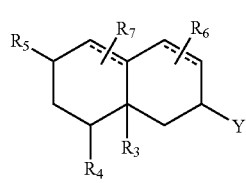

Formula II where Y is 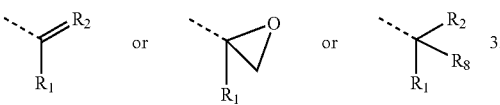

and, similar to the R-groups of Formula I, $R_1$, $R_2$, $R_3$, $R_4$, $R_5$, $R_6$, $R_7$, and $R_8$ are each independently H, =O, —OH, lower aliphatic, lower aliphatic alcohol, lower aliphatic thiol, carbonyl containing lower aliphatic, thiocarbonyl containing lower aliphatic, lower aliphatic ether, or lower aliphatic epoxide. Additionally, the eremophilane ring structures of compounds described by Formula II may contain double-bonds as described with respect to Formula I.

The compounds of Formula II form a subset of the compounds described in Formula I, and all chemical substitutions and modifications discussed in relation to Formula I are possible at the corresponding structure positions on Formula II. For example, the substitutions and modifications discussed in relation to $R_7$ of Formula I correspond to $R_5$ of Formula II. As another example, the substitutions and modifications discussed in relation to $R_5$, $R_6$, and $R_8$, of Formula I correspond to $R_7$ of Formula II, and the substitutions and modifications discussed in relation to, $R_{11}$, $R_3$ and $R_4$ of Formula I correspond to $R_6$ of Formula II. As yet another example, the substitutions and modifications discussed in relation to $R_1$, $R_2$, and $R_{12}$ of Formula I correspond to $R_1$, $R_2$, and $R_8$ of Formula II, respectively, and the substitutions and modifications discussed in relation to $R_9$, and $R_{10}$ of Formula I correspond to $R_4$ and $R_8$ of Formula II, respectively.

In some embodiments, a compound according to Formula II is a specific stereoisomer, such as:

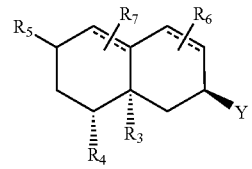

In some embodiments, lower aliphatic is a lower alkyl; lower aliphatic alcohol is a lower alkyl alcohol; lower aliphatic thiol is a lower alkyl thiol; lower aliphatic carboxylic acid is a lower alkyl carboxylic acid; carbonyl containing lower aliphatic is a lower carbonyl containing alkane; thiocarbonyl containing lower aliphatic is a lower thiocarbonyl containing alkane; lower aliphatic ether is a lower alkane ether; and lower aliphatic epoxide is a lower alkane epoxide.

In some embodiments, $R_3$, $R_4$, $R_5$, $R_6$, $R_7$, and $R_8$, are independently =O, —OH, lower aliphatic alcohol, carbonyl containing lower aliphatic, lower aliphatic ether, or lower aliphatic epoxide. In alternative embodiments, several of $R_3$, $R_4$, $R_5$, $R_6$, $R_7$, and $R_8$, are substituents and the others are H. For example, $R_3$, $R_4$, and $R_5$ can be substituents and the others H. In particular embodiments, $R_5$ is =O, —OH, lower aliphatic, lower aliphatic alcohol, carbonyl-containing lower aliphatic, lower aliphatic ether, or lower aliphatic epoxide. In more particular embodiments, $R_5$ is =O, or —OH and $R_3$, and $R_4$ are lower aliphatic, such as lower alkyl (e.g., methyl or ethyl).

In some embodiments, Y is

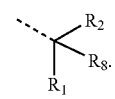

In particular embodiments, one of the bonds carbon-$R_1$ or carbon-$R_2$ is a double bond and $R_8$ is absent. In more particular embodiments, the carbon-$R_2$ bond is a double bond and $R_8$ is absent.

In some embodiments, $R_1$, $R_2$, and $R_8$ are independently H, =O, —OH, lower aliphatic (for example, lower alkyl), lower aliphatic alcohol (for example, lower alkyl alcohol), lower aliphatic ether (for example, lower alkyl ether) or lower aliphatic epoxide (for example, lower alkyl epoxide). In particular embodiments, $R_2$ is O and the carbon-$R_2$ bond is a double bond. In even more particular embodiments, $R_1$ is lower aliphatic alcohol, such as a lower alkyl alcohol (e.g., —CH$_2$OH) or lower aliphatic, such as lower alkyl (e.g., methyl or ethyl).

In some embodiments, Y is

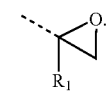

In particular embodiments, $R_1$ is H, —OH, lower aliphatic (for example, lower alkyl), lower aliphatic alcohol (for example, lower alkyl alcohol), lower aliphatic ether (for example, lower alkyl ether) or lower aliphatic epoxide (for example, lower alkyl epoxide). In even more particular embodiments, $R_1$ is lower aliphatic alcohol, such as lower alkyl alcohol (e.g., —$CH_2OH$) or lower aliphatic, such as lower alkyl (e.g., methyl or ethyl).

In some embodiments, Y is

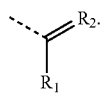

In particular embodiments, $R_1$ is independently H, —C═O, —OH, lower aliphatic (for example, lower alkyl), lower aliphatic alcohol (for example, lower alkyl alcohol), lower aliphatic ether (for example, lower alkyl ether) or lower aliphatic epoxide (for example, lower alkyl epoxide); and $R_2$ is independently O, S, lower aliphatic (for example, lower alkyl), lower aliphatic alcohol (for example, lower alkyl alcohol), lower aliphatic ether (for example, lower alkyl ether) or lower aliphatic epoxide (for example, lower alkyl epoxide). In particular embodiments, $R_2$ is O. In even more particular embodiments, $R_1$ is lower aliphatic alcohol, such as a lower alkyl alcohol (e.g., —$CH_2OH$) or lower aliphatic, such as lower alkyl (e.g., methyl or ethyl).

In some embodiments, $R_6$ and $R_7$ form an epoxide group at $C_1$ and $C_{10}$ on the eremophilane ring structure, similar to the joining of $R_5$ and $R_6$ at $C_1$ and $C_{10}$ described with respect to Formula I. In such embodiments, compounds described by Formula II are based on the structure:

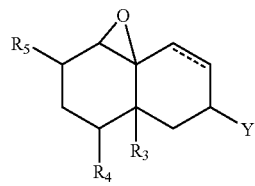

Certain other exemplary pesticidal eremophilane sesquiterpenes are represented by Formula III:

Formula III

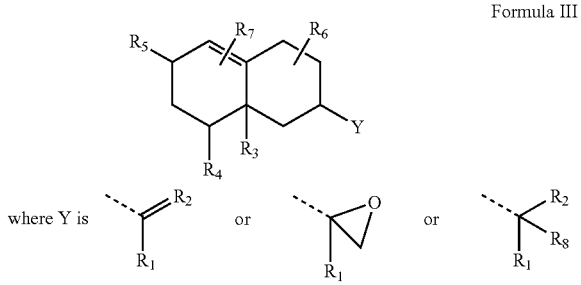

where Y is and, similar to the R-groups of Formula I, $R_1$, $R_2$, $R_3$, $R_4$, $R_5$, $R_6$, $R_7$, and $R_8$ are each independently H, ═O, —OH, lower aliphatic, lower aliphatic alcohol, lower aliphatic thiol, carbonyl containing lower aliphatic, thiocarbonyl containing lower aliphatic, lower aliphatic ether, or lower aliphatic epoxide. Additionally, the eremophilane ring structures of compounds described by Formula III may contain double-bonds as described with respect to Formulas I and II.

The compounds of Formula III form a subset of the compounds described by Formulas I and II, and all chemical substitutions and modifications discussed in relation to Formulas I and II are possible at the corresponding structure positions on Formula III.

In some embodiments, a compound according to Formula III is a specific stereoisomer, such as:

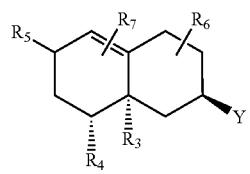

In some embodiments, lower aliphatic is a lower alkyl; lower aliphatic alcohol is a lower alkyl alcohol; lower aliphatic thiol is a lower alkyl thiol; lower aliphatic carboxylic acid is a lower alkyl carboxylic acid; carbonyl containing lower aliphatic is a lower carbonyl containing alkane; thiocarbonyl containing lower aliphatic is a lower thiocarbonyl containing alkane; lower aliphatic ether is a lower alkane ether; and lower aliphatic epoxide is a lower alkane epoxide.

In some embodiments, $R_3$, $R_4$, $R_5$, $R_6$, $R_7$, and $R_8$, are independently ═O, —OH, lower aliphatic alcohol, carbonyl containing lower aliphatic, lower aliphatic ether, or lower aliphatic epoxide. In alternative embodiments, several of $R_3$, $R_4$, $R_5$, $R_6$, $R_7$, and $R_8$, are substituents and the others are H. For example, $R_3$, $R_4$, and $R_5$ can be substituents and the others H. In particular embodiments, $R_5$ is ═O, —OH, lower aliphatic, lower aliphatic alcohol, carbonyl-containing lower aliphatic, lower aliphatic ether, or lower aliphatic epoxide. In more particular embodiments, $R_5$ is ═O, or —OH and $R_3$, and $R_4$ are lower aliphatic, such as lower alkyl (e.g., methyl or ethyl).

In some embodiments, Y is

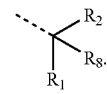

In particular embodiments, one of the bonds carbon-$R_1$ or carbon-$R_2$ is a double bond and $R_8$ is absent. In more particular embodiments, the carbon-$R_2$ bond is a double bond and $R_8$ is absent.

In some embodiments, $R_1$, $R_2$, and $R_8$ are independently H, ═O, —OH, lower aliphatic (for example, lower alkyl), lower aliphatic alcohol (for example, lower alkyl alcohol), lower aliphatic ether (for example, lower alkyl ether) or lower aliphatic epoxide (for example, lower alkyl epoxide). In particular embodiments, $R_2$ is O and the carbon-$R_2$ bond is a double bond. In even more particular embodiments, $R_1$ is lower aliphatic alcohol, such as a lower alkyl alcohol (e.g., —$CH_2OH$) or lower aliphatic, such as lower alkyl (e.g., methyl or ethyl).

In some embodiments, Y is

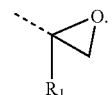

In particular embodiments, $R_1$ is H, —OH, lower aliphatic (for example, lower alkyl), lower aliphatic alcohol (for example, lower alkyl alcohol), lower aliphatic ether (for example, lower alkyl ether) or lower aliphatic epoxide (for example, lower alkyl epoxide). In even more particular embodiments, $R_1$ is lower aliphatic alcohol, such as lower alkyl alcohol (e.g., —$CH_2OH$) or lower aliphatic, such as lower alkyl (e.g., methyl or ethyl).

In some embodiments, Y is

In particular embodiments, $R_1$ is independently H, —C=O, —OH, lower aliphatic (for example, lower alkyl), lower aliphatic alcohol (for example, lower alkyl alcohol), lower aliphatic ether (for example, lower alkyl ether) or lower aliphatic epoxide (for example, lower alkyl epoxide); and $R_2$ is independently O, S, lower aliphatic (for example, lower alkyl), lower aliphatic alcohol (for example, lower alkyl alcohol), lower aliphatic ether (for example, lower alkyl ether) or lower aliphatic epoxide (for example, lower alkyl epoxide). In particular embodiments, $R_2$ is O. In even more particular embodiments, $R_1$ is lower aliphatic alcohol, such as a lower alkyl alcohol (e.g., —$CH_2OH$) or lower aliphatic, such as lower alkyl (e.g., methyl or ethyl).

Certain other exemplary pesticidal eremophilane sesquiterpenes are represented by Formula IV:

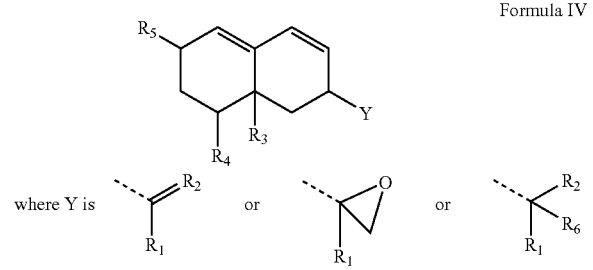

and, similar to the R-groups of Formula I, $R_1$, $R_2$, $R_3$, $R_4$, $R_5$, and $R_6$ are each independently H, =O, —OH, lower aliphatic, lower aliphatic alcohol, lower aliphatic thiol, carbonyl-containing lower aliphatic, thiocarbonyl-containing lower aliphatic, lower aliphatic ether, or lower aliphatic epoxide.

The compounds described by Formula IV form a subset of the compounds described by Formulas I and II. All chemical substitutions and modifications discussed in relation to Formulas I and II are possible at the corresponding positions on Formula IV.

In some embodiments, a compound according to Formula IV is a particular stereoisomer, such as:

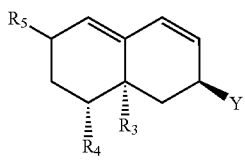

Other exemplary pesticidal eremophilane sesquiterpenes are represented by Formula V:

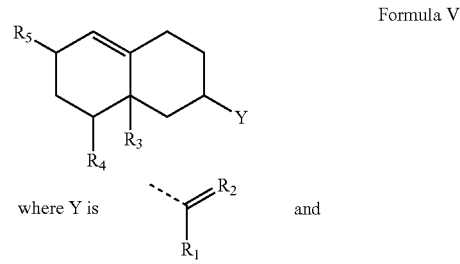

$R_1$ is lower alkyl, lower alkyl alcohol, or carbonyl-containing lower alkyl; $R_2$ is lower alkyl, or O; $R_3$ is lower alkyl; $R_4$ is lower alkyl; and $R_5$ is H, —OH, =O; lower alkyl alcohol, or carbonyl-containing lower alkyl; or Y is

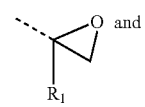

$R_1$ is lower alkyl, lower alkyl alcohol, or carbonyl-containing lower alkyl; $R_3$ is lower alkyl; $R_4$ is lower alkyl; and $R_5$ is H, —OH, =O; lower alkyl alcohol, or carbonyl-containing lower alkyl; or Y is

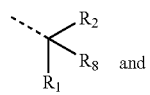

$R_1$ is H, =O, —OH, lower alkyl, lower alkyl alcohol, lower alkyl ether, lower alkyl aldehyde, lower alkyl ketone, or lower alkyl epoxide; $R_2$ is H, =O, —OH, lower alkyl, lower alkyl alcohol, lower alkyl ether, lower alkyl aldehyde, lower alkyl ketone, or lower alkyl epoxide; $R_3$ is lower alkyl; $R_4$ is lower alkyl; and $R_5$ is H, —OH, =O; lower alkyl alcohol, carbonyl-containing lower alkyl; $R_8$ is H, —OH, lower aliphatic, or lower aliphatic alcohol. However, if either the carbon-$R_1$ or carbon-$R_2$ is a double bond, then $R_8$ is absent. For example, in some embodiments, the carbon-$R_2$ bond is a double bond, such as embodiments where $R_2$ is O, the carbon-$R_2$ bond is a double bond, and $R_1$ is a lower alkyl alcohol (e.g., —$CH_2OH$) or lower alkyl (e.g., methyl or ethyl).

The compounds described by Formula V form a subset of the compounds described by Formulas I and II, and all chemical substitutions and modifications discussed in relation to Formulas I and II are possible at the corresponding structure positions on Formula V.

In some embodiments, a compound according to Formula V is a particular stereoisomer, such as:

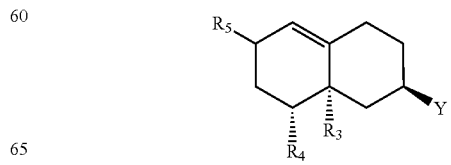

In some embodiments, $R_3$ is lower alkyl, such as methyl. In some examples, $R_4$ is lower alkyl (such as methyl) or lower alkyl alcohol (such as —$CH_2OH$). In some examples, $R_5$ is H. In other embodiments, $R_5$ is H or —OH, Y is

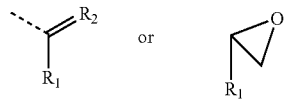

and $R_1$ is lower alkyl, such as methyl or ethyl, or lower alkyl alcohol, such as ethyl alcohol.

In other embodiments, Y is

and $R_1$ is lower alkyl alcohol or lower alkyl alcohol. In such embodiments, $R_3$ and $R_4$ may independently be lower alkyl, and $R_5$ may be H.

In other embodiments, Y is

$R_1$ is lower alkyl alcohol and $R_2$ is O or lower alkyl. In such embodiments, $R_3$ and $R_4$ may independently be methyl, and $R_5$ may be H.

Still other exemplary pesticidal eremophilane sesquiterpenes are represented by Formula VI:

Formula VI

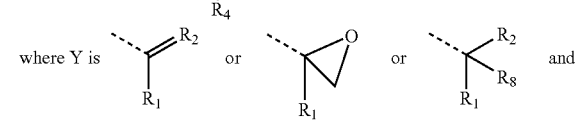

and, similar to the R-groups of Formula I, $R_1$, $R_2$, $R_3$, $R_4$, $R_5$, and $R_8$ are each independently H, =O, —OH, lower aliphatic, lower aliphatic alcohol, lower aliphatic thiol, carbonyl-containing lower aliphatic, thiocarbonyl-containing lower aliphatic, lower aliphatic ether, or lower aliphatic epoxide.

The compounds described by Formula VI form a subset of the compounds described by Formulas I and II, and all chemical substitutions and modifications discussed in relation to Formulas I and II are possible at the corresponding structure positions on Formula VI.

In some embodiments, a compound according to Formula VI is a particular stereoisomer, such as:

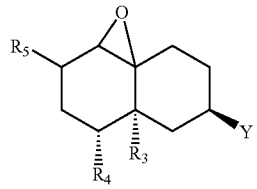

In particular embodiments, Y is

and $R_1$ is lower alkyl or lower alkyl alcohol; $R_2$ is lower alkyl, or O; $R_3$ is lower alkyl; $R_4$ is lower alkyl; and $R_5$ is H, —OH, or =O.

In other particular embodiments, Y is

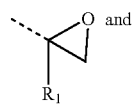

$R_1$ is lower alkyl or lower alkyl alcohol; $R_3$ is lower alkyl; $R_4$ is lower alkyl; and $R_5$ is H, —OH, or =O.

In still other particular embodiments, Y is

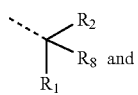

$R_1$ is H, =O, —OH, lower alkyl, lower alkyl alcohol, lower alkyl ether, or lower alkyl epoxide; $R_2$ is H, =O, —OH, lower alkyl, lower alkyl alcohol, lower alkyl ether, or lower alkyl epoxide; $R_3$ is lower alkyl; $R_4$ is lower alkyl; $R_5$ is H, —OH, or =O; and $R_8$ is H, —OH, lower alkyl, or lower alkyl alcohol. However, if either the carbon-$R_1$ or carbon-$R_2$ is a double bond, then $R_8$ is absent. For example, in some embodiments, the carbon-$R_2$ bond is a double bond. In even more particular embodiments, $R_2$ is O, the carbon-$R_2$ bond is a double bond, and $R_1$ is a lower alkyl alcohol (e.g., —$CH_2OH$) or lower alkyl (e.g., methyl or ethyl).

While some of the compounds encompassed by Formulas I-VI are known—for example, valencene, nootkatol, epinootkatol, and nootkatone—many other compounds are novel. Examples of novel compounds include, but are not limited to, 13-hydroxy-valencene, valencene-11,12-epoxide, valencene-13-aldehyde, and nootkatone-1,10-11,12-diepoxide.

Valencene, nootkatol, epinootkatol, nootkatone, and nootkatene are commercially available and may be isolated from natural sources. For example, nootkatone may be prepared according to the methods and processes of U.S. Pat. No. 5,847,226 and WO 97/22575A1, and valencene and nootkatone may be obtained from Bedoukian Research Inc., of Danbury, Conn. These compounds are known to be nontoxic to humans and non-human animals. For example, nootkatone is used as a fragrance and food flavoring.

The compounds described by Formulas I, II, III, IV, V and/or VI, including 13-hydroxy-valencene, valencene-11,12-epoxide, valencene-13-aldehyde, and nootkatone-1,10-11,12-diepoxide, may be isolated from natural sources, such as Alaska yellow Cedar, *Alpinia* species, bitter cardamom, and citrus fruits (e.g., grapefruit), may be semi-synthesized from compounds isolated from such natural sources, or may be completely synthesized. Example 1 provides one method for isolating compounds from Alaska yellow cedar, and Examples 11-14 illustrate semi-synthesis of the compounds.

Compounds described herein may be described by their common names, numerical compound identifiers, or IUPAC names. Certain, non-limiting exemplary compounds are listed in Table 1.

TABLE 1

| Common Name | Number | IUPAC Name |
|---|---|---|
| valencene | compound 5 | 4βH,5α-eremophlia-1(10),11-diene |
| nootkatene | compound 6 | 4βH,5α-eremophlia-1,9,11-triene |
| nootkatone | compound 7 | 4βH,5α-eremophlia-1(10),11-dien-2-one |
| 13-hydroxy-valencene | compound 10 | 4βH,5α-eremophlia-1(10)-ene |
| nootkatol | compound 12 | 2α-hydroxy-4βH,5α-eremophlia-1(10),11-dien |
| valencene-11,12-epoxide | compound 13 | 11,12-epoxy-4βH,5α-eremophlia-1(10)-ene |
| valencene-13-aldehyde | compound 15 | 4βH,5α-eremophlia-1(10),11-diene-13-ol |
| nootkatone-11,12-epoxide | compound 16 | 11,12-epoxy-4βH,5α-eremophlia-1(10)-en-2-one |
| nootkatone-1,10-epoxide | compound 17 | 1,10-epoxy-4βH,5α-eremophlia-11-en-2-one |
| nootkatone-1,10-11,12-diepoxide | compound 18 | 1,10-(11,12)-diepoxy-4βH,5α-eremophlia-2-one |

Compounds 10, 13, 15, and 18 (13-hydroxy-valencene, valencene-11,12-epoxide, valencene-13-aldehyde, and nootkatone-1,10-11,12-diepoxide) are understood to be novel compounds.

In some embodiments, the addition of oxygen-containing groups increases the bioactivity of the compound. Exemplary oxygen-containing groups include double-bond oxygen moities and hydroxy-containing or carbonyl-containing groups, such as $=O$, $-OH$, lower aliphatic alcohol (such as methyl alcohol or ethyl alcohol), lower aliphatic carboxylic acid, carbonyl-containing lower aliphatic (such as a ketone or aldehyde), lower aliphatic ether, or lower aliphatic epoxide. In other embodiments, the addition of R-groups containing hydrogen-bonding atoms or functional groups, including both hydrogen bond donors and hydrogen bond acceptors, increases the bioactivity of the compound. It is understood that some R-groups may be both oxygen-containing groups and hydrogen-bond donors or acceptors. Additionally, sulfur-containing group analogous to the oxygen-containing groups (where the group contains a sulfur atom in the position otherwise occupied by an oxygen atom) described herein increase the bioactivity of compounds in some embodiments.

Tables 2 and 3 present particular embodiments of compounds according to Formula I:

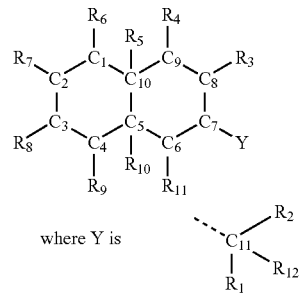

Formula I

In the exemplary compounds listed in Table 2, the $C_1$-$C_{10}$ bond is a double bond and $R_5$ is absent. Additionally, some of these compounds also are encompassed and may be described by Formula II, III, IV, V and/or VI.

TABLE 2

| | Compound 51 | Compound 52 | Compound 53 | Compound 54 | Compound 55 |
|---|---|---|---|---|---|
| $R_1$ | $CH_2OH$ | $CH_2OH$ | $CH_2OH$ | $CH_2OH$ | $CH_3$ |
| $R_2$ | $CH_3$ | $CH_3$ | $CH_2OH$ | $CH_2OH$ | $CH_3$ |
| $R_3$ | H | H | H | H | H |
| $R_4$ | H | H | H | H | H |
| $R_6$ | H | H | H | H | H |
| $R_7$ | $=O$ | OH | H | $=O$ | OH |
| $R_8$ | H | H | H | H | H |
| $R_9$ | $CH_3$ | $CH_3$ | $CH_3$ | $CH_3$ | $CH=O$ |
| $R_{10}$ | $CH_3$ | $CH_2OH$ | $CH=O$ | $CH_2OH$ | $CH_3$ |
| $R_{11}$ | H | H | H | H | H |
| $R_{12}$ | OH | H | H | OH | OH |

| | Compound 56 | Compound 57 | Compound 58 | Compound 59 | Compound 60 |
|---|---|---|---|---|---|
| $R_1$ | $CH_2OH$ | $CH_3$ | $CHOCH_3$ | $CH_2CH=CH_3$ | $CH_2CH_2COOH$ |
| $R_2$ | CHO | $COCH_3$ | $CH_3$ | $CH_2COOH$ | $CH_2OH$ |
| $R_3$ | H | H | H | H | H |
| $R_4$ | H | H | H | H | H |
| $R_6$ | H | H | H | H | H |
| $R_7$ | $=O$ | OH | H | OH | H |
| $R_8$ | H | H | H | H | H |
| $R_9$ | $CH_2OH$ | $CH=O$ | $CH=O$ | $CH_2OH$ | $CH_3$ |
| $R_{10}$ | $CH_3$ | $CH=O$ | $CH_3$ | $CH_2OH$ | $CH=O$ |
| $R_{11}$ | H | H | H | H | H |
| $R_{12}$ | H | OH | $CH_2CH_2OH$ | $CH_2COOH$ | H |

TABLE 3

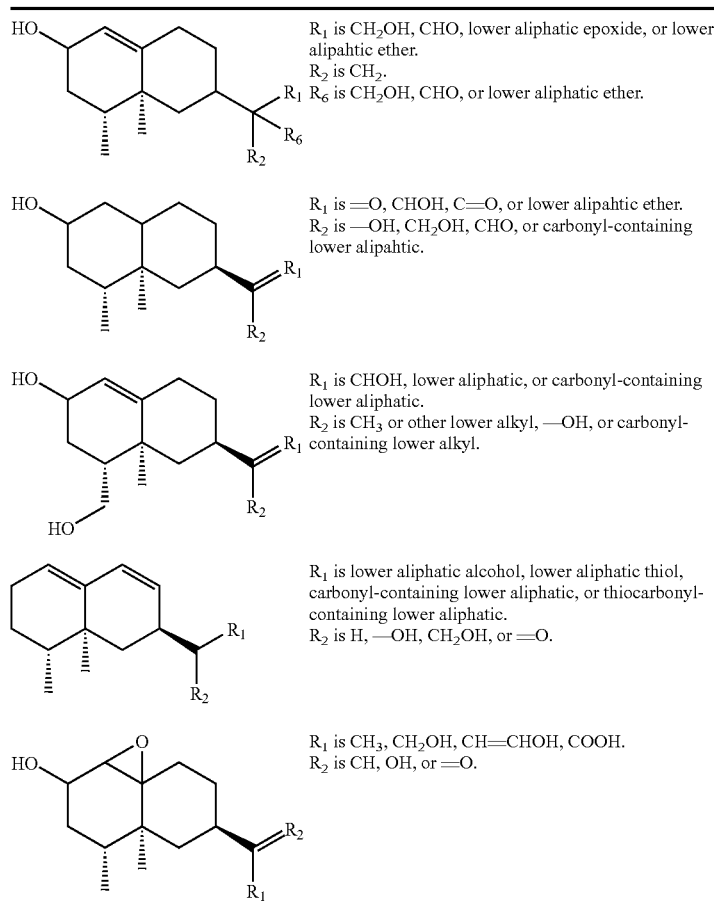

R₁ is CH₂OH, CHO, lower aliphatic epoxide, or lower alipahtic ether.
R₂ is CH₂.
R₆ is CH₂OH, CHO, or lower aliphatic ether.

R₁ is =O, CHOH, C=O, or lower alipahtic ether.
R₂ is —OH, CH₂OH, CHO, or carbonyl-containing lower alipahtic.

R₁ is CHOH, lower aliphatic, or carbonyl-containing lower aliphatic.
R₂ is CH₃ or other lower alkyl, —OH, or carbonyl-containing lower alkyl.

R₁ is lower aliphatic alcohol, lower aliphatic thiol, carbonyl-containing lower aliphatic, or thiocarbonyl-containing lower aliphatic.
R₂ is H, —OH, CH₂OH, or =O.

R₁ is CH₃, CH₂OH, CH=CHOH, COOH.
R₂ is CH, OH, or =O.

As illustrated by the exemplary compounds of Tables 1-3, particular embodiments employ compounds where $R_1$ and $R_2$ are independently lower alkyl, lower alcohol, or lower alkenyl; $R_3$, $R_4$, and $R_6$ are H; $R_7$ is H, —OH, or =O; $R_8$ is H; $R_9$ and $R_{10}$ are independently lower alkyl, lower alcohol, or lower aldehyde; $R_{11}$ is H; and $R_{12}$ is H, —OH, lower alcohol, or carbonyl-containing lower alkyl.

Specific examples of compounds encompassed by Formulas I-VI include those listed in Table 4, though this list of compounds is merely representative and not exhaustive.

TABLE 4

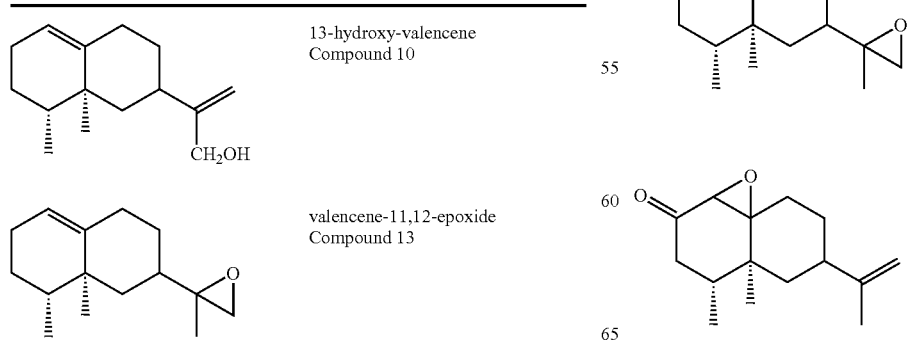

13-hydroxy-valencene
Compound 10 valencene-11,12-epoxide
Compound 13

TABLE 4-continued

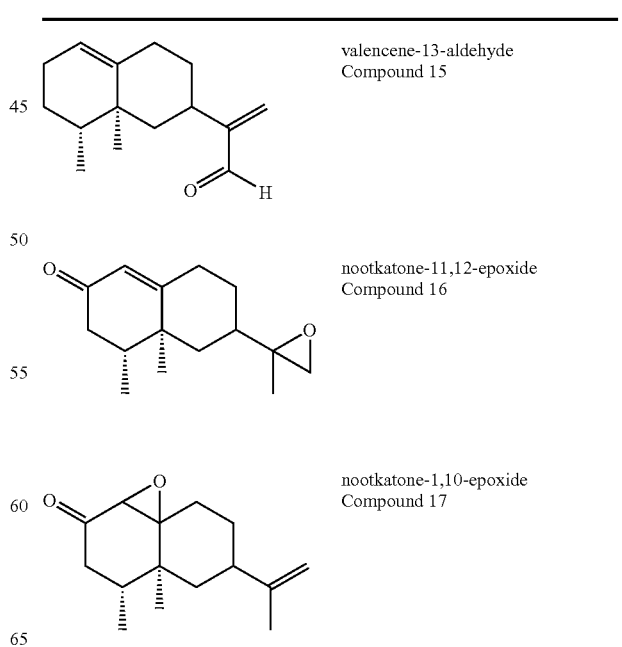

valencene-13-aldehyde
Compound 15 nootkatone-11,12-epoxide
Compound 16 nootkatone-1,10-epoxide
Compound 17

TABLE 4-continued

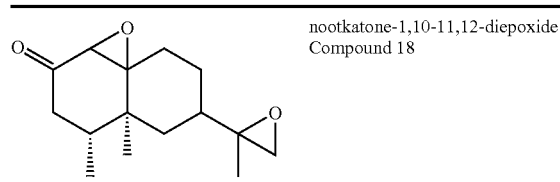

nootkatone-1,10-11,12-diepoxide
Compound 18

Pesticidally Acceptable Salts and Compositions

All compounds described herein may be used in pure form or in the form of a pesticidally acceptable salt. Pesticidally acceptable salts of the compound of any of Formulas I-VI may be salts of organic or inorganic acids, such as hydrochloric acid, hydrobromic acid, sulfuric acid, nitric acid, perchloric acid, phosphoric acid, formic acid, acetic acid, trifluoroacetic acid, oxalic acid, malonic acid, toluenesulfonic acid, benzoic acid, terpenoid acids (e.g., abiotic acid), or natural phenolic acids (e.g., gallic acid and its derivatives). Additionally, the compound of any of Formulas I-VI may be included as an active ingredient within a composition, for example, a pesticide or pest control agent, in a free form or in the form of a a pesticidally acceptable salt.

A pesticidal composition includes one or more of the above-described compounds and a pesticidally acceptable carrier, additive, or adjuvant, and the pesticidal composition may function as a pesticide or pest control agent.

Such pesticidal compositions may be in the form of a solid, liquid, gas, or gel. If a solid composition is created, suitable solid carriers include agriculturally useful and commercially available powders. Liquid compositions may be aqueous or non-aqueous, depending on the needs of the user applying the pesticidal composition, and liquids may exist as emulsions, suspensions, or solutions. Exemplary compositions include (but are not limited to) powders, dusts, granulates, topical oils, encapsulations, emulsifiable concentrates, suspension concentrates, directly sprayable or dilutable solutions, coatable pastes, dilute emulsions, wettable powders, soluble powders, dispersible powders, or fumigants.

The particle or droplet size of a particular composition may be altered according to its intended use. The pesticidal composition also may include an apparatus for containing or dispersing the compound or composition, such as a storage kit, fumigant bottle (such as the commonly named "flea bomb"), or insect trap.

Pesticidally acceptable carriers, additives, and adjuvants include stabilizers, preservatives, antioxidants, extenders, solvents, surfactants, antifoaming agents, viscosity regulators, binders, tackers, or other chemical agents, such as fertilizers, antibiotics, fungicides, nematicides, or herbicides. Such carriers, additives, and adjuvants may be used in solid, liquid, gas, or gel form, depending on the embodiment and its intended application. Pesticidally acceptable adjuvants are those materials that assist or enhance the action of a compound or composition. Surfactants and antifoaming agents are just two examples of pesticidally acceptable adjuvants. However, any particular material may alternatively function as a "carrier," "additive," or "adjuvant" in alternative embodiments, or may fulfill more than one function.

Certain additives, carriers, or adjuvants may be active or inactive materials or substances. In some instances, the efficacy of a composition may be increased by adding one or more other components that minimize toxicity to hosts or increase the anti-pest effect of the composition.

Additionally, the composition may include plural pesticidal compounds. Such a composition includes a compound as described herein and a second pesticidal compound, and the second pesticidal compound also may be a compound as described herein, or may be any other type or class of pesticide (e.g., an organophosphate or pyrethrin).

In certain compositions, the second pesticidal compound, additive, carrier, or adjuvant provides a synergistic effect by increasing the efficacy of the pesticidal composition more than the additive amount. As just one, non-limiting example, a composition containing both 1% nootkatone and 1% 13-hydroxy-valencene by weight that is more than twice as effective—such as four times as effective or ten times as effective—than a composition containing only 1% nootkatone or 1% 13-hydroxy-valencene by weight demonstrates a synergistic effect.

The following list of exemplary carriers, additives, and adjuvants is meant to be illustrative, not exhaustive.

Suitable solid carriers, such as those used for dusts and dispersible powders, include natural mineral fillers such as calcite, talcum, kaolin, montmorillonite, and attapulgite. Highly dispersed silicic acids or highly dispersed absorbent polymers may be added to such carriers. Granulated materials of inorganic or organic nature may be used, such as dolomite or pulverized plant residues. Suitable porous granulated adsorptive carriers include pumice, broken brick, sepiolite, and bentonite. Additionally, nonsorbent carriers, such as sand, may be used. Some solid carriers are biodegradable polymers, including biodegradable polymers that are digestible or degrade inside an animal's body over time.

Suitable liquid carriers, such as solvents, may be organic or inorganic. Water is one example of an inorganic liquid carrier. Organic liquid carriers include vegetable oils and epoxidized vegetable oils, such as rape seed oil, castor oil, coconut oil, soybean oil and epoxidized rape seed oil, castor oil, coconut oil, soybean oil, and other essential oils. Other organic liquid carriers include silicone oils, aromatic hydrocarbons, and partially hydrogenated aromatic hydrocarbons, such as alkylbenzenes containing 8 to 12 carbon atoms, including xylene mixtures, alkylated naphthalenes, or tetrahydronaphthalene. Aliphatic or cycloaliphatic hydrocarbons, such as paraffins or cyclohexane, and alcohols, such as ethanol, propanol or butanol, also are suitable organic carriers. Gums, resins, and rosins used in forest products applications and naval stores (and their derivatives) also may be used. Additionally, glycols, including ethers and esters, such as propylene glycol, dipropylene glycol ether, diethylene glycol, 2-methoxyethanol, and 2-ethoxyethanol, and ketones, such as cyclohexanone, isophorone, and diacetone alcohol may be used. Strongly polar organic solvents include N-methylpyrrolid-2-one, dimethyl sulfoxide, and N,N-dimethylformamide.

Suitable surfactants may be nonionic, cationic, or anionic, depending on the nature of the compound used as an active ingredient. Surfactants may be mixed together in some embodiments. Nonionic surfactants include polyglycol ether derivatives of aliphatic or cycloaliphatic alcohols, saturated or unsaturated fatty acids and alkylphenols. Fatty acid esters of polyoxyethylene sorbitan, such as polyoxyethylene sorbitan trioleate, also are suitable nonionic surfactants. Other suitable nonionic surfactants include water-soluble polyadducts of polyethylene oxide with polypropylene glycol, ethylenediaminopolypropylene glycol and alkylpolypropylene glycol. Particular nonionic surfactants include nonylphenol polyethoxyethanols, polyethoxylated castor oil, polyadducts of polypropylene and polyethylene oxide, tributylphenol polyethoxylate, polyethylene glycol and octylphenol polyethoxylate. Cationic surfactants include quaternary ammonium salts carrying, as N-substituents, an 8 to 22 carbon straight or branched chain alkyl radical. The quaternary ammonium salts carrying may include additional substituents, such as unsubstituted or halogenated lower alkyl, benzyl, or hydroxy-lower alkyl radicals. Some such salts exist in the form of halides, methyl sulfates, and ethyl sulfates. Particular salts include stearyldimethylammonium chloride and benzyl bis(2-chloroethyl)ethylammonium bromide. Suitable anionic surfactants may be water-soluble soaps as well as water-soluble synthetic surface-active compounds. Suitable soaps include alkali metal salts, alkaline earth metal salts, and unsubstituted or substituted ammonium salts of higher fatty acids. Particular soaps include the sodium or potassium salts of oleic or stearic acid, or of natural fatty acid mixtures. Synthetic anionic surfactants include fatty sulfonates, fatty sulfates, sulfonated benzimidazole derivatives, and alkylarylsulfonates. Particular synthetic anionic surfactants include the sodium or calcium salt of ligninsulfonic acid, of dodecyl sulfate, or of a mixture of fatty alcohol sulfates obtained from natural fatty acids. Additional examples include alkylarylsulfonates, such as sodium or calcium salts of dodecylbenzenesulfonic acid, or dibutylnaphthalenesulfonic acid. Corresponding phosphates for such anionic surfactants are also suitable.

The concentration of a compound, such as a compound according to any of Formulas I-VI, which serves as an active ingredient, may vary according to particular compositions and applications. In a number of embodiments, the percentage by weight of the active ingredient will be from about 0.1% to about 90%. A suitable amount for a particular application may be determined using bioassays for the particular pest intended to be controlled. Higher concentrations are usually employed for commercial purposes or products during manufacture, shipment, or storage; such embodiments have concentrations at least about 10%, or from about 25% to about 90% by weight. Prior to use, a highly concentrated formulation may be diluted to a concentration appropriate for the intended use, such as from about 0.1% to 10%, or from about 1% to 5%. In any such formulation, the active ingredient may be a compound according to any of Formulas I-VI, a corresponding pesticidally acceptable salt, or a mixture thereof.

The compounds have deterrent, repellent, and/or toxic effects on certain pest targets and may function as pest repellents or pest control agents, as well as pesticides. Certain compounds have a lethal effect on specific pests. Unlike a number of commercially available pesticides, many compositions have an active ingredients (such as a compound according to Formula I, II, III, IV, V and/or VI) that are substantially nontoxic to humans and domesticated animals and that have minimal adverse effects on wildlife and the environment.

The efficacy of a subject compound or composition is determined from an adverse effect on the pest population, including (but not limited to) physiological damage to a pest, inhibition or modulation of pest growth, inhibition or modulation of pest reproduction by slowing or arresting proliferation, inhibition or complete deterrence of pest movement into a locus, initiation or promotion of pest movement away from a locus, inhibition or elimination of pest feeding activity, or death of the pest, all of which are encompassed by the term "controlling." Thus, a compound or composition that controls a pest (i.e., a pest control agent or pesticide) adversely affects its presence, status, and/or physiological condition at a locus. The efficacy and quantity of a pesticidally effective amount for a given compound may be determined by routine screening procedures employed to evaluate pesticidal activity and efficacy, such as those screening described in the Examples.

Efficacy and appropriateness of a compound also may be assessed by treating an animal, plant, or environmental locus with a compound or composition described herein and observing the effects on the infesting pest population and any harm to plants or animals contacted by the compound, such as phytotoxicity to plants, toxicity to animals, or dermal sensitivity to animals. For example, in certain embodiments, compounds or compositions are directly applied to a host plant or animal actually or potentially infested with a pest. In such embodiments, the efficacy of the compound or composition may be monitored by examining the state of host or environmental locus infestation by the pest population before and after application in light of physiological damage to an animal or plant host infected by the pest population found within the environmental locus. Additionally, the appropriateness of a compound or composition may be assessed by observing any adverse effects to the person applying the composition to an infested plant, animal, or environmental locus. In particular embodiments, the effective amount of a compound or composition meets the mortality, modulation, or control criteria above, and has minimal or no adverse effect on plants, non-human animals, or humans that may come into contact with the compound or composition.

The compounds and compositions have a broad range of biocidal effects, such as pesticidal activity against one or more pests, and certain compounds and/or compositions may be more effective on some pests than others. Some compounds according to any of Formulas I-VI, or compositions containing such compounds, may be partially or totally ineffective against some pests at certain concentrations. However, any differences in efficacy should not in any way detract from the utility of these compounds or compositions, or their methods of use, since some of these compounds or compositions may function as broad, general acting pesticides, while other compounds or compositions may function as specific or selective pesticides. The Examples set forth below illustrate methods by which the degree of selectivity of pesticidal activity may be readily ascertained.

The subject compounds and compositions offer several advantages over currently used pesticides. These naturally-occurring compounds may be isolated from a variety of plant sources, including Alaska yellow cedar and grapefruit, and generally exhibit a very high $LD_{50}$ against non-arthopod animals. Thus, these compounds are relatively nontoxic to humans, domesticated animals and livestock, birds, fish, and other wildlife.

The compounds and compositions described herein may be used to control or eliminate crop pests (and may be used up to harvest), to control the growth of pests on harvested crops and stored foods, and for controlling pests in natural and artificial environments. The compound or composition may be applied to plant and animal parts (e.g., skin, fur, feathers, scales, leaves, flowers, branches, fruits) and to objects within an environment that come into contact with a pest. Additionally, the compound or composition may be included as part of an object held or placed upon a prospective host plant or animal to inhibit pest infestation, such as a collar, clothing, or supporting mechanism (e.g., a stake supporting a seedling tree, a rose trellis, or a cage for supporting a tomato plant).

The compounds and compositions have useful inhibitory and/or curative properties in the field of pest control, even at low concentrations, and may be used as part of an integrated pest management (IPM) program. These and other methods of using the compounds and compositions are further described below.

The compounds and compositions function as topical or ingestible toxins effective against all developmental stages of arthropod pests, such as insects and acarines (i.e., members of taxonomic orders Insecta and Acarina). The onset of the pesticidal action of the compounds and compositions may follow directly (e.g., kill a pest within a short amount of time) or onset of pesticidal action may occur some time after the pest has initially contacted the compound or composition.

Methods of Use

The compounds and compositions according to any of Formulas I-VI may be used as pesticides, including acaricides and insecticides, or may be used as agents to control pests, such as pest repellents. Some embodiments of using these compounds and compositions cover a range of applications involving humans, non-human animals (including domesticated companion animals, livestock, and wildlife), and plants, including recreational, veterinary, agricultural, silvicultural, horticultural, and environmental applications. Other embodiments encompass disease control applications, such as controlling the spread of disease among animals and/or plants by controlling the vector for that disease. Exemplary vector-borne diseases of animals include, but are not limited to: Lyme disease; Dengue Fever; Yellow Fever; tick borne-babesiosis; tuleremia; powassan-like virus infection; tick borne encephalitis; relapsing fever; malaria; encephalitis, such as the disease caused by the West Nile Virus, Eastern equine encephalitis, St. louis encephalitis, Venezuelan equine encephalitis, Western equine encephalitis and Lacrosse encephalitis; Colorado Tick Fever; ehrlichiosis; Rocky Mountain Spotted Fever; and the Plague. An exemplary, non-limiting vector-borne disease of plants is Dutch Elm disease, elm yellows phytoplasmas, and apply powdery mildew are non-limiting examples of vector-borne diseases of plants.

In any particular embodiment, the compound or composition is administered in a pesticidally effective amount. That amount may depend on a variety of factors, including (but not limited to) the area to be treated, the pest to be treated, its metabolism, its behavior (e.g., feeding habits, breeding, daily or seasonal activity cycles, development, nesting habits, etc.), and behavior of the host the pest infests.

In some embodiments, the compound or composition is applied once, while alternative embodiments employ plural applications of the same or different compounds or compositions. In particular embodiments, the compound or composition is administered on an hourly, daily, weekly, monthly, quarterly, or annual basis. In any particular embodiment, the frequency of application may be regular or irregular, and the time elapsed between successive applications may be the same or different. For example, and without limitation, the compounds or compositions may be applied every eight to twelve hours; four times per day at irregular intervals; every evening; four times per week; every other day; every other week; every other month; twice a month; every three months; every six months; every nine months; or annually. Like the amount of the compound or composition used in an embodiment, the frequency and number of applications of that compound or composition may depend on a variety of factors, including (but not limited to) the area to be treated, the pest to be treated, its metabolism, and its behavior (e.g., feeding habits, breeding, daily or seasonal activity cycles, development, nesting habits, etc.), and behavior of the host the pest infests.

Included are embodiments where a compound or composition described above is applied to a particular human, non-human animal, plant, inanimate object, or environmental locus. The compound or composition may be applied directly to the pest, thus causing the pest to directly contact the compound, or may be applied to some locus or host that is expected to come into contact with the pest.

If applied to a locus, the compound may be applied to the locus generally, such as by an aerosol or fumigant, or applied to a human, non-human animal, plant, or inanimate object within that locus. The size of a particular locus may vary considerably according to the method of application. For example, in area-wide applications, the compound is dispersed over a locus of an environment, rather than intentionally directed at a particular pest, human, plant, or inanimate object. The locus of an area-wide application may be several hundred to thousands of acres, if the compound is used for agricultural spraying or to control the spread of a vector-borne disease; in structural applications, such as controlling pests within a home or restaurant, the locus may be several hundred several thousand square feet. However, in personal, veterinary, or horticultural applications, such as using topical pest repellent spray or ointment, or using a flea shampoo to bathe a pet, the locus may be limited to the area in the immediate vicinity of the animal, plant, or human host.

The size of the locus also may vary according to such factors as the intended application, presence of humans or non-human animals, level of human or non-human activity within the locus, type of formulation embodying the compound or composition, and environmental factors, such as wind speed, humidity, temperature, and anticipated rainfall.

Methods of application include spraying, atomizing, dusting, immersing, coating, dressing, scattering, and pouring. In particular embodiments, the compound or composition is provided or administered to a human or non-human animal, such as oral administration (for example, as a pill, powder, tablet, capsule, or food supplement), intravenous injection, percutaneous injection, or topical treatment. In more particular embodiments, the composition is a topical oil, lotion, or cream and the compound is absorbed through the skin. A particular method of application may be selected in accordance with the intended objectives of and circumstances related to a particular use.

The frequency of application also may depend on the residual action of the particular compound or composition. "Residual action" refers to the length of time a compound or composition may exist in a particular environment and remain effective. For example, one particular compound lasts approximately 11 weeks in a protected environment before it begins to degrade and lose effectiveness. See Example 5 below. A person using a compound, such as using a pesticidal composition having this compound as an effective ingredient to control ants, could apply the compound to some locus in a protected environment, such as a household basement, every 11 weeks.

Some formulations embodying compounds and compositions according to any of Formulas I-VI may offer certain advantages, such as long term effect due to extended residual action, or high levels of safety and efficacy for veterinary, agricultural, and nuisance pest applications.

The compounds and compositions described herein may be employed in formulations intended for use in public or private homes, residences, businesses, restaurants, hospitals, or other similar places of human activity. In such embodiments, the formulations may be used to kill or repel pests, such as mosquitoes, ants, spiders, or roaches, and may be applied directly to the pests or a locus the pest is expected to contact. For example, flea bomb or other fumigant containing an active ingredient in the form of a compound according to any of Formulas I-VI could be used within a home, such as applied within a particular room of a home, to control fleas. As another example, a commercial spray containing an active ingredient in the form of a compound according to any of Formulas I-VI could be applied to the floors and other interior spaces of a restaurant to control cockroaches. In any such embodiment, the formulation may kill or repel a pest by directly contacting the pest, may be induced into the atmosphere of the locus, or may be applied to a human, non-human animal, plant, or inanimate object (e.g., the surface of a floor) expected to come into contact with the pest.

Certain embodiments employ formulations for use on humans, non-human animals, or plants for their protection. For example, certain formulations may be insecticides and/or acaricides sprayed onto the leaves of indoor plants for controlling aphids. Other formulations may embody compounds or compositions according to any of Formulas I-VI as lotions or oils that repel pests.

Certain embodiments encompass protection of homes, buildings, or other structures from nuisance insects, such as termites, cockroaches, and ants. In such methods, the compound or composition may be applied to a locus within or outside the structure protected, such as spraying onto floors or inside cupboards, or soaking the ground outside the structure. Additionally, the compound or composition may be embedded within materials used to construct the structure, such as siding, wall studs, or beams.

Certain nontoxic compounds and compositions may be used to control pests parasitic to a particular subject. The subject may be a human or non-human animal, including domesticated animals and livestock, such as dogs, cats, birds, reptiles, cattle, swine, sheep, fowl, and goats. In such embodiments, the compound or composition may be provided to the human or non-human animal as a topical formulation, such as a cream, lotion, ointment, dip, shampoo, spotting liquid or spray, or provided in the form of a wearable product, such as a collar, ear tag, or piece of clothing. The compound or composition may be administered orally, rectally, or by injection, such as by a pill, solution, subcutaneous injection, or subcutaneous implant. In any such application, the frequency of treatment of the subject to be treated by the compound or composition is generally from about once per week to about once per year, such as from about once every two weeks to about once every six months, or from about once per month to about once every three months. The appropriate dose provided or administered in a particular embodiment may vary according to the efficacy of the particular compound or composition; intended biocidal spectrum of the compound or composition; the physiological state or health of the subject, including allergic indications of the subject; and environmental considerations, such as exposure to wind, rain, heat, or cold. Suitable doses include from about 1 to 500 mg/kg (mg of compound or composition per kg body weight of the host), such as from about 1 to about 100 mg/kg, from about 1 to about 50 mg/kg, from about 5 to about 50 mg/kg, from about 5 to about 10 mg/kg, from about 10 to about 100 mg/kg, or less than 1 mg/kg.

The compound or composition may be used to clean the animal, such as by an owner bathing or placing a flea collar on a pet, or in veterinary applications. Cleaning an animal may be distinguished from treating an animal body, since an animal in good health would not require substantial treatment to correct a deficiency of health.

In certain embodiments, the compounds or compositions applied in an area-wide manner, such as in protection of agricultural crops described below. In addition to agricultural applications, area-wide applications may include silvicultural, horticultural, or other forms of environmental pest management and control. In such embodiments, a compound or composition may be applied to plant foliage, such as spraying or dusting, or applied to the soil, such as drenching a particular locus with a liquid formulation or applying the active ingredient in solid form to a locus. In some instances, plants within or adjacent to the locus of application may absorb the active ingredient or composition through their roots. In other instances, the active ingredient will remain in the environment, such as when a compound or composition is applied to a stagnant body of water to control mosquito larvae.

Certain embodiments use the compounds and compositions described herein for pest control in food production and storage. For example, certain compositions may be used as agricultural pesticides to control pests and protect grain, vegetable, herb, spice, or fruit crops. Compositions also may be used to control pests affecting other plants useful or important in agricultural or horticultural production, such as those plants or crops producing cotton, flax, tobacco, hemp, rubber, nuts, nursery stock, and ornamental plant parts.

The compounds and compositions according to any of Formulas I-VI may be used to protect plant products not only during growth and production, but also during storage or transport of such products. For example, some embodiments use compounds or compositions to protect grain stored in silos, bales of cotton or tobacco stored in warehouses, or bushels of fruit being transported from an orchard.

The compounds and compositions described herein also may be used to protect plant propagation material, such as seeds, fruit, tubers, or plant cuttings. The propagation material may be treated with the formulation before planting, such as soaking, coating, or dressing seeds prior to sowing. The compounds and compositions also may be applied to the soil where the propagation material will be planted, such as in-furrow application to protect seeds.

In such applications, the compound or composition may be applied to provide a certain concentration of the compound in the environment at a particular locus. That certain concentration may be measured, established, or determined according to the needs of the user. For example, when applying the compound or composition to crops, the rate of application may depend on the nature of soil, the type of application (e.g., spraying crop foliage, burial in soil), the crop plant to be protected, the pest to be controlled, the prevailing climatic conditions, growing season, proximity to residential areas or protected environments, and other factors. As another example, when applying the compound or composition to stored or transported agricultural products, the rate of application may depend on the localized environment (e.g., storage within a warehouse, storage under a covered shelter, transport within a trailer), expected duration of storage, product to be protected, the pest to be controlled, economic considerations, and other factors. In certain embodiments, the rates of concentration are in the range from about 0.01 to about 1000 ppm (parts-per-million), such as from about 0.1 to about 500 ppm, of active ingredient. In area-wide applications, rates of application per hectare may be from about 0.5 g/ha to 2000 g/ha, such as particularly from about 10 to 1000 g/ha, or from about 20 to 600 g/ha. As one non-limiting example, pesticides for the control of mosquito vectors of malaria may be used in area-wide applications at a rate of application of about 70 g/ha to about 1.15 kg/ha.

Use of pesticides is regulated in the United States by state and federal agencies, including the Environmental Protection Agency (EPA) and Food and Drug Administration (FDA). Relevant regulatory programs include the Federal Insecticide, Fungicide and Rodenticide Act (FIFRA) and the Federal Food, Drug and Cosmetic Act (FD&C Act). Certain articles of manufacture in accordance with these governmental and regulatory considerations may be made using compounds or compositions according to any of Formulas I-VI.

In such embodiments, a pesticidally active compound according to any of Formulas I-VI is embodied in an acceptable carrier and stored within a container capable of storing the composition for its shelf life. The container may be made of any suitable material such as plastic or other polymer, glass, metal, or the like. Printed instructions and/or a printed label indicating that the composition may be used to control pests are associated with this container. The instructions and/or label may provide information regarding the use of the composition for pesticidal purposes in accordance with the treatment method set forth herein and may be associated with the container by being adhered to the container, or accompanying the container in a package. The label may indicate the composition is approved for use as a pesticide, and the instructions may specify the pests intended to be controlled by the composition, the method and rate of application, dilution protocols, use precautions, and the like. Additionally, the container may include a feature or device for applying the composition to the pest population or locus to be treated. For example, if the article of manufacture includes a liquid composition, the feature or device may be a hand-operated, motorized, or pressurized pressure-driven sprayer. In certain embodiments, the article of manufacture includes, packaged together, a vessel—such as a tube, barrel, bottle, bottle, or can—containing the composition and instructions for use of the composition for controlling a pest. In other embodiments, the article of manufacture is a device that includes the compound as part of the device, such as a surface coated with the compound, for example a bait trap or flea collar. In alternative embodiments, the article of manufacture includes packaging material containing the composition. Additionally, the packaging material may include a label indicating that the composition may be used for controlling a pest and, in particular embodiments, a pesticide for killing a pest. Examples of articles of manufacture include, but are not limited to, spray bottles of a ready-to-use formulation for household use; bottles, cans, or barrels containing concentrated formulations that may be diluted for area-wide applications; containers of concentrated formulations for use in industrial settings; flea collars or ear tags for domesticated companion animals and livestock; bottles or kits for shampooing, dipping, or cleaning domesticated companion animals or livestock; a bottle containing a formulation for human use as a shampoo or body wash; plastic tubules containing a topical oil for applying to a domesticated animal; and rodent bait boxes or host targeted bait boxes containing a pesticidal composition for killing ectoparisites infesting the host animal.

EXAMPLES

The following examples are provided to illustrate particular features of certain embodiments. The scope of the invention should not be limited to those features exemplified.

Example 1

Isolating Certain Compounds from Alaska Yellow Cedar

This example illustrates one method of isolating pesticidal ermorphilane sesquiterpenes from Alaska yellow cedar (*Chamaecyparis nootkatensis*), including nootkatone, 13-hydroxy-valencene, and valencene-11,12-epoxide.

Alaska Cedar Tree

An Alaska cedar tree was collected from the Hunqry Mountain area on the Sol Duc River drainage on the western slopes of the Olympic Mountains in the Olympic National Forest. A botanical voucher specimen (#188046) is deposited in the Oregon State University Herbarium. The heartwood was separated from sapwood and bark and then chipped in a grinder to approximately 15×10 mm chips and stored at room temperature until used.

Extraction of the Essential Oils

Steam Distillation

Steam distillation of the heartwood chips was carried out in a standard apparatus, in which 1.5 kg of chips were steam distilled for 6-12 hours to yield 26 grams of essential oil. The oil was recovered by extraction of the combined water/oil distillate with diethyl ether. The diethyl ether solution was dried over anhydrous sodium sulfate and evaporated on a rotary evaporator under reduced pressure, resulting in a yellow oil. Nootkatin tended to crystallize out in the condenser during distillation, so diethyl ether was periodically used to dissolve these crystals into the oil fraction. Nootkatin crystallized out of the Alaska cedar oil when it was placed in the refrigerator. These crystals were recovered by decanting the oil and re-crystallization of the nootkatin from the oil solution to give pure material. The remaining Alaska cedar oil that was used in this study was substantially free of nootkatin with only trace amounts of nootkatin present.

Extraction by Diethyl Ether 200 grams of Alaska cedar heartwood chips were twice extracted with 3 liters of diethyl ether for 24 hours at room temperature to ensure complete extraction of the oil. The combined ether solution was filtered, dried with anhydrous sodium sulfate, and evaporated to give 2.2 grams of an oil.

Isolation of Compounds

Isolation from the Steam Distilled Oil:

The essential oil components were separated and purified by traditional column chromatography. When packing a column, a degased slurry of solvent and adsorbent (Kieselgel 60 $PF_{254}$ Silica gel, Germany) was poured into a glass column with a diameter and height determined by sample size. The solvent was drained until its level was just over the top of adsorbent. The stopper of the column was closed and the column was ready for use.

The distilled oil (62 grams) was dissolved in 50 ml of hexane and chromatographed over a Silica gel 60 column (7×45 cm) using a gradient solvent mixture of hexane and diethyl ether from 100% hexane to 60:40 (hexane/diethyl ether, v/v). Aliquots of 20 mL eluent were collected with a Gilson FC-100 fraction collector and monitored by TLC developed with dichloromethane. The plates were visualized under UV light and subsequently sprayed with acidic vanillin solution, followed by heating. Aliquots of eluent with same component checked by TLC were combined together to form one fraction. Seven major fractions were obtained after the first chromatographing of the crude distilled oil (62 g): I (11.31 g), II (20.6 g), III (0.48 g), IV (18.03 g), V (3.45 g), VI (5.08 g), VII (1.13 g).

Fraction I was found to mainly contain valencene and nootkatene and a trace of methyl carvacrol by gas chromotography.

Fraction II was highly pure carvacrol checked by gas chromotography.

Fraction III was a mixture of trace components by comparing its chromatogram to that of the crude oil in gas chromotagraphy.

Fraction IV showed two main spots on a TLC plate developed by dichloromethane, one visible under UV light and the other only after being sprayed with acidic vanillin solution, followed by heating. Their Rf values were 0.29 and 0.42, respectively. This fraction was analyzed by gas chromotography and found to consist of nootkatone (Rf 0.29) and one unknown compound named "unknown compound 1," Rf 0.42. A portion of this fraction (5 g) was rechromatographed twice over a Kieselgel column (5×45 cm) with dichloromethane as mobile phase and yielded the two pure compounds, nootkatone (1.55 g) and unknown compound 1 (0.68 g). As shown in FIG. 1A, unknown compound 1 was subsequently identified as 13-hydroxy-valencene.

Fraction V was still a mixture, which contained small amount of almost every component in the crude oil.

Fraction VI checked by gas chromotography and TLC was found to contain one main compound (Rf 0.43 in hexane/ethyl acetate 70/30 v/v). This unknown compound 2 (8 mg) was yielded from one portion of this fraction (30 mg) after preparative HPLC procedures and, as shown in FIG. 1A, later identified as nootkatol.

Fraction VII contained highly pure unknown compound 2 (nootkatol) checked by gas chromotography.

Figure 1B:
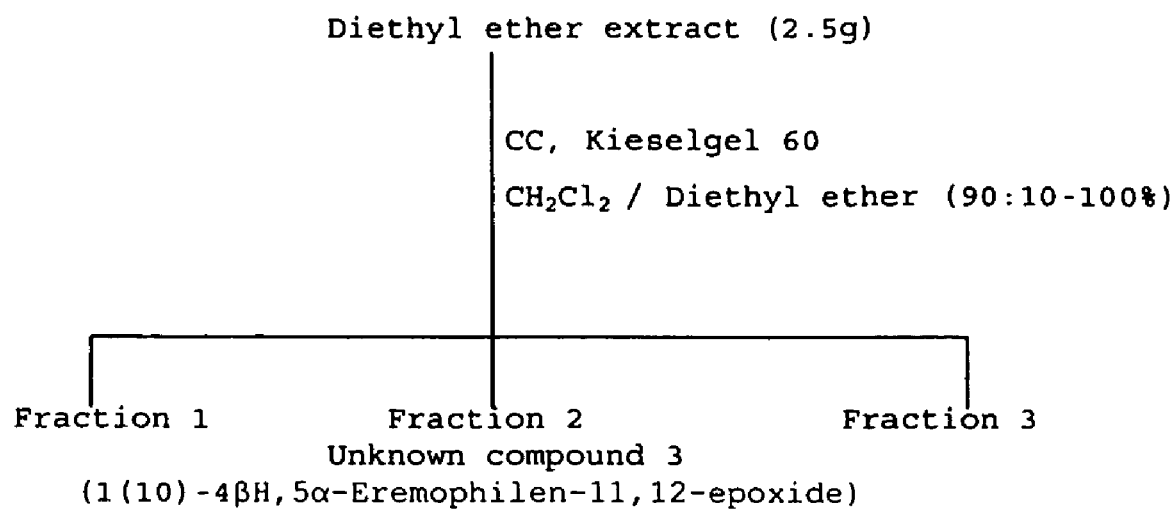

A graphic representation of separation of these fractions is illustrated in FIGS. 1A and 1B.

Isolation from the Diethyl Ether Extract:

The diethyl ether extract (2.5 g) was chromatographed on a Silica gel column (5×44 cm) with diethyl ether and dichloromethane as the gradient solvent system from 90:10 (dichloromethane:diethyl ether, v/v) to 100% diethyl ether. See FIG. 1. Another unknown compound, named "unknown compound 3," was obtained as Fraction 2. As shown in FIG. 1B, unknown compound 3 was later identified as valencene-11, 12-epoxide.

Spectroscopic Data for Isolated Compounds

Eremophil-1(10),11-dien-13-ol. Isolated from Fraction IV of the crude essential oil extraction and originally listed as "unknown compound 1" but later identified as eremophil-1(10),11-dien-13-ol. See FIG. 1A. Pale yellowish oil. MW=220. High Resolution MS revealed mass (220.18271) and formula ($C_{15}H_{24}O$). $C_{15}H_{24}O$ requires 220.18272. $[\alpha]_{589}$+61.9 (C 2.26 in chloroform). Rf 0.42 (in dichloromethane). MS (70 ev), m/z 220([M$^+$] 100), 202(40), 189 (81), 161(77), 105(67), 91(65), 79(54). $^{13}$C NMR (ppm): 154.5, 143.2, 120.8, 108.3, 65.7, 45.8, 41.3, 38.3, 37.1, 34.0, 33.1, 27.5, 26.3, 18.8, 16.0. $^1$H NMR (δ): 0.87 (3H, d, J=6 Hz), 0.95 (3H, s), 1.01 (1H, d, J=12.6 Hz), 1.21 (1H, dd, J=4.1, 13.3 Hz), 1.41 (3H, m), 1.59 (1H, m), 1.82 (1H, dm?), 1.93 (1H, m), 2.01 (2H, m), 2.09 (1H, ddd, J=14.0, 4.16, 2.66 Hz), 2.31 (1H, tt, J=12.7, 3.0 Hz), 4.12 (2H, s), 4.88 (1H, s), 5.02 (1H, s), 5.33 (1H, t, J=2.4 Hz), 7.26, (1H, s).

Nootkatone. Pale yellowish oil. MW=218, $C_{15}H_{22}O$. $[\alpha]_{589}$+152 (1.51 in chloroform). Rf 0.29 (in dichloromethane). $^{13}$C NMR (ppm): 199.7, 170.6, 149.0, 124.6, 109.2, 43.9, 42.0, 40.4, 40.3, 39.3, 33.0, 31.6, 20.8, 16.8, 14.8. $^1$H NMR (δ): 5.77 (1H, s), 4.74 (2H), d), 1.74 (3H, s), 1.13 (3H, s), 0.97 (3H, s).

Nootkatol. Colorless oil. MW=220. High Resolution MS revealed mass (220.18165) and formula ($C_{15}H_{24}O$). $C_{15}H_{24}O$ requires 220.18272. $[\alpha]_{589}$+41.3 (C 1.52 in chloroform). Rf 0.43 (in hexane/ethyl acetate), 0.4 (in hexane/diethyl ether 50:50 v/v), 0.74 (in dichloromethane/diethyl ether 50:50 v/v). MS (70 ev), m/z 220([M$^+$] 100), 203(21), 187(4), 177(60), 162(6), 138(13), 121(20), 107(21), 93(22), 81(16), 67(13). $^{13}$C NMR (ppm): 150.6, 146.5, 124.7, 108.9, 68.4, 45.0, 41.2, 39.7, 38.6, 37.6, 33.3, 32.8, 21.2, 18.6, 15.8. $^1$H NMR (δ): 0.89 (3H, d, J=6.9 Hz), 0.95 (1H, J=2.7 Hz?), 0.99 (3H, s), 1.20 (1H, dm, J=4.3 Hz), 1.37 (1H, td, J=12.4, 10.0 Hz), 1.51 (1H, m, J=2.1), 1.71 (3H, s), 1.76 (1H, td, J=2.0, 6.5 Hz), 1.79 (1H, dd, J=2.0, 4.5), 1.85 (1H, dd, J=12.6, 2.7 Hz), 2.1 (1H, ddd, J=14.1, 4.2, 2.6 Hz), 2.25 (1H, tt, J=12.4, 3.0 Hz), 2.33 (1H, m), 4.25 (1H, m), 4.68 (2H, m), 5.32 (1H, d, J=1.6 Hz).

valencene-11,12-epoxide. Isolated from Fraction 2 of the diethyl ether extract and originally listed as "unknown compound 3," but later identified as valencene-11,12-epoxide. See FIG. 1B. Dark yellow oil. MW=220. High Resolution MS revealed mass (220.18280) and formula ($C_{15}H_{24}O$). $C_{15}H_{24}O$ requires 220.18272. $[\alpha]_{589}$+58.5 (C 1.17 in chloroform). Rf 0.36 (in dichloromethane/diethyl ether 50:50 v/v). MS (70 ev), m/z 220([M$^+$] 85), 189(74), 178(6), 161(100), 135(41), 121(25), 107(38), 81(42), 75(44). $^{13}$C NMR (ppm): 143.4, 120.5, 75.0, 69.0, 41.5, 40.4, 39.9, 38.1, 32.9, 29.6, 27.6, 26.3, 20.4, 18.8, 16.1. $^1$H NMR (δ): 0.86 (1H, m), 0.89 (3H, d, J=6.27 Hz), 0.93 (3H, s), 1.00 (1H, dd, J=4.7, 13.2 Hz), 1.07 (3H, s), 1.42 (3H, m), 1.71 (1H, ddd, J=2.6, 4.7, 12.2 Hz), 1.84 (1H, tt, J=3.0, 12.6 Hz), 1.98 (3H, m), 2.07 (1H, ddd, J=2.6, 4.2, 14.1 Hz), 2.27 (1H, m), 3.43 (1H, d, J=10.14 Hz), 3.59 (1H, d, J=11.28 Hz), 5.32 (1H, t, J=2.5 Hz).

NMR experiments were run on a Bruker Model AM 400 spectrometer with the XWINNMR software package, using CDCl$_3$ as the solvent and TMS as an internal standard for chemical shifts given in ppm. DEPT (Distortionless Enhancement by Polarization Transfer) experiments were performed using both pulses of 135° C. and 90° C. $^1$H-$^1$H COSY, $^1$H-$^{13}$C HSQC, HMBC, NOEs were also performed on the instrument according to the standard procedures described by Bruker. EI-MS was done with a Kratos MS-50TC mass spectrometer.

A gas chromatograph (GC-17A Shimadzu, Japan) was used for monitoring composition of fractions and identifying pure compounds by using standards. The gas chromatograph was equipped with a flame ionization detector (FID). The column (30 m×0.25 mm DB-5, 0.25 µm, J&W Scientific) was temperature programmed from 100° C. for 1 minute, then to 150° C. at a rate of 5° C./min, then to 220° C. at 3° C./min, and finally to 240° C. at 5° C./min and held at that temperature for 2 minutes.

GC-MS analysis was carried out on a HP 5972 GC/MS to confirm those previously known compounds in Alaska cedar heartwood oil. One microliter of a 587 ng/µl solution of the distillate dissolved in hexane was injected into the injector maintained at 250° C. A 30 m×0.25 mm ID DB-5 column was used and temperature programmed from 50° C. initially held for 5 minutes to 300° C. finally at a rate of 5° C./min. The transfer line temperature was 280° C. The MS was operated in electron impact mode with a 70 eV ionization potential and was scanned from 50-560 m/z.

The optical rotations were measured on a digital polarimeter (JASCO, MODEL DIP-370, Japan) with a Na lamp (589 nm) as the light source. Chloroform was used as the solvent.

Analytical thin-layer chromatography (TLC) was performed on aluminum plates pre-coated with Kieselgel 60 F$_{254}$ (EM, Germany) to monitor the course of column separation and act for a preliminary guideline to select mobile phase for column separation.

The solvent systems used for TLC analysis were:

(1) Hexane:Ethyl acetate (70:30 v/v)

(2) Dichloromethane (3) Hexane:Diethyl ether (50:50 v/v)

The spots on TLC plates were visualized under UV light and sprayed with acidic vanillin solution (1 g vanillin, 50 mL absolute EtOH, and 10 mL concentrated HCl), followed by heating.

Preparative HPLC was performed on a Waters Millipore Model 510 system using a normal phase column (Silica-prep, 250×10 mm 10 μm, Phenomenex). Degased hexane (A) and ethyl acetate (B) were used as the gradient mobile phase, starting from 15 up to 30% B in 20 min, to 40% B in 30 min. The total flow rate was maintained at 3.5 mL/min. An UV detector (Lambda-Max Model 481 LC spectrophotometer, Waters Millipore) was connected to the outlet of the column and operated at 254 nm and 0.01 AUFS. A computer-based data system (Maxima 820) was connected to the system for monitor and control. Fractions were collected according to the peaks shown on the screen.

A Buchi Rotavapor Model R-110 equipped with a Buchi 461 Water Bath was used for the removal of solvent from the samples under reduced pressure by using a water aspirator. The temperature of water in the bath was maintained at 30° C.

All solvents used were ACS grades and re-distilled prior to use. All water was also distilled before use.

Example 2

Pesticidal Properties of Certain Compounds on Ticks and Fleas

Samples of the compounds listed below were obtained from Dr. Karchesy, a co-inventor, and screened for biocidal activities against nymphal *Ixodes scapularis*. In this example, 2% acetone solutions (wt./vol.) of the compounds were applied to inner surfaces of 2-dram friction cap vials. Vials and caps were treated then allowed to dry for a minimum of 4 hours before placing 10 nymphs in each container. These same vials were used to challenge additional nymphs and adult *I. scapularis* ticks and adult *Xenopsylla cheopis* fleas through five weeks to observe any possible residual activity. Results of this biocidal screening are presented in Table 5.

TABLE 5

| Compound | I. scapularis nymphs (24 h) | I. scapularis nymphs (72 h) | I. scapularis adults (4 wk) | X. cheopis adults (5 wk) |
| --- | --- | --- | --- | --- |
| Valencene | 10/10 | 0/5 | 0/5 | 0/5 |
| Nootkatene | 10/10 | 4/5 | 0/5 | 0/5 |
| Nootkatone | 10/10 | 5/5 | 5/5 | 5/5 |
| valencene-11,12-epoxide | 10/10 | 5/5 | 5/5 | 5/5 |
| Nootkatin | 1/10 | 0/5 | 0/5 | 0/5 |

Numbers in parentheses refer to length of treatment in terms of hours (h) or weeks (wk). Data is presented in terms of number killed/number tested. For test periods longer than 24 hours, the treated vials were allowed to sit for the stated period after drying (72 h, 4 wk, or 5 wk) and each group of arthropods was added to the vials for the final 24 h of the test period.

These bioassays demonstrate that four of the five compounds had biocidal activity against ticks and fleas and that nootkatone and valencene-11,12-epoxide were the most efficacious and persistent.

Example 3

Pesticidal Properties of Certain Compounds on Mosquito

Using a bioassay method similar to that presented in Example #2, the susceptibility of *Aedes aegypti* adults to the five compounds presented in Example #2 at 24 hours challenge was determined to be 100% mortality except for nootkatin (20% mortality).

Example 4

Pesticidal Properties of Nootkatol on Certain Arthropods

Nootkatol was tested using the bioassay presented in Example 2. The biocidal activity of nootkatol was determined to be essentially equivalent to the activity of nootkatene against ticks, fleas and mosquitoes.

Example 5

Persistence of Biocidal Activity of the Compounds

Persistence of biocidal activity was determined for nootkatone and valencene-11,12-epoxide by using the vials as treated with the 2% solutions of Example 2. This bioassay employed groups of ticks, fleas, formicids and termites using a method similar to that presented in Example 2. Each group of arthropods demonstrated 100% mortality after 24 hour exposure at each test through 10 weeks for both chemicals. At 11 weeks, the biocidal activity began to dissipate below the 100% mortality level.

Example 6

Comparison of Extracted Nootkatone Samples

Two nootkatone samples were compared to nootkatone isolated from Alaska yellow cedar using the method presented in Example 1. The first sample was a natural extract of nootkatone taken from grapefruit oil purchased commercially. The second sample was a synthetically produced nootkatone purchased commercially.

Both samples were compared to the nootkatone originating from Alaska yellow cedar in terms of their biocidal activities. Using a bioassay method similar to that presented in Example 2, no differences were discernible among the nootkatone samples in terms of their biocidal effect on ticks, fleas and mosquitoes.

Example 7

Effectiveness of Compounds Against Ticks

Baseline dose-mortalities were established for nymphal *I. scapularis* for nootkatone and valencene-11,12-epoxide using the method described in Maupin, G. O., and Piesman, J., J. Med. Entomol., 31: 319-21 (1994).

A comparison of relative potency was made with published data for carbaryl and permethrin (Maupin and Piesman, 1994)

and Alaska yellow cedar essential oil (Panella et al., J. Med. Entomol. 34: 340-45 (1997) is presented in Table 6.

TABLE 6

| Compound | $LD_{50}$ |
|---|---|
| Essential oil of Alaska yellow cedar | $151.0 \times 10^{-3}$ |
| Nootkatone | $4.2 \times 10^{-3}$ |
| 13-hydroxy-valencene | $4.1 \times 10^{-3}$ |
| Carbaryl | $7.2 \times 10^{-3}$ |
| Permethrin | $3.0 \times 10^{-3}$ |

Nootkatone and valencene-11,12-epoxide were extracted from Alaska yellow cedar essential oil. Both compounds were approximately 50 times more potent and about 98% more effective against nymphal ticks than their parent source, essential oil of Alaska yellow cedar. While permethrin and carbaryl demonstrated greater effectiveness than these two biocidal sesquiterpenes, this relative potency is not absolutely accurate since the permethrin and carbaryl samples were technical grade (>99% pure), while the two biocidal sesquiterpenes were extracted at a 90-95% purity level.

Example 8

Effectiveness of Compounds Against Mosquito

The susceptibility of mosquitoes to valencene-11,12-epoxide was determined using a method similar to that presented in Example 2. *Culex p. pipiens* was treated with serial dilutions of valencene-11,12-epoxide from 0.125% down to 0.0045%. Due to the extreme sensitivity of this species to the biocidal activity of valencene-11,12-epoxide, the corresponding $LD_{50}$ could not be calculated by Probit analysis. At the lowest tested dosage, the mortality rate was still 64%. Therefore, the $LD_{50}$ for compound 10 against *C. pipiens* is $<4.5 \times 10^{-3}$. Similar results were obtained when both valencene-11,12-epoxide and nootkatone were assayed for their biocidal activities against *Aedes aegypti*, thus demonstrating that mosquitoes are quite sensitive to these compounds. Table 7 compares the effectiveness of raw essential oil of Alaska yellow cedar, nootkatone, and valencene-11,12-epoxide against two mosquitoes, *A. aegypti* and *C. pipiens*.

TABLE 7

| Compound | *A. aegypti* $LD_{50}$ | *C. pipiens.* $LD_{50}$ |
|---|---|---|
| Essential oil of Alaska yellow cedar | $32.0 \times 10^{-3}$ | $61.0 \times 10^{-3}$ |
| Nootkatone | $<4.5 \times 10^{-3}$ | $<4.5 \times 10^{-3}$ |
| valencene-11,12-epoxide | $<4.5 \times 10^{-3}$ | $<4.5 \times 10^{-3}$ |

Example 9

Effectiveness of Compounds Against Ticks, Fleas, and Mosquitoes

The pesticidal activities of valencene-11,12-epoxide, valencene-13-aldehyde, nootkatone-1,10-epoxide, and nootkatone-1,10-11,12-diepoxide against ticks, fleas, and mosquitoes were assayed.

Materials and Methods.

Plant Extracts. All compounds were produced in the Forest Chemistry Laboratory at Oregon State University (Corvallis, Oreg.) from an Alaska yellow cedar (*Chamaecyparis nootkatensis*) specimen collected under a special collection permit from the United States Forest Service. A plant voucher specimen (#188046) was deposited at Oregon State University Herbarium (Corvallis, Oreg.).

Some tested compounds—carvacrol, nootkatin, nootkatene, valencene, nootkatone, nootkatol, and 13-hydroxy-valencene—were isolated from the steam distilled essential oil of Alaska yellow cedar heartwood (see Example 1). Valencene-11,12-epoxide was isolated from the diethyl ether extract of the ground heartwood. See Xiong, Y., *Essential oil components of Alaska cedar heartwood* (Masters Thesis, Oregon State University, Corvallis, Oreg., 2001). Valencene-13-aldehyde was prepared by oxidation of valencene with $SeO_2$. Nootkatone-1,10-epoxide and nootkatone-1,10-11,12-diepoxide were prepared from nootkatone with $H_2O_2$, and nootkatone-11,12-epoxide was prepared using m-chloroperbenzoic acid. Commercial samples of nootkatone for comparison were obtained from Bedoukian Research, Inc., Danbury, Conn. (semi-synthetic crystalline) and Frutarom, Inc. N.J. (from grapefruit oil). As shown in Table 8, each compound was assigned a numerical identifier for this Example (the identifiers for the compounds used in this Example may be different than the identifiers used elsewhere in this application as specified in Table 1 above). The compounds identified by an asterisk—nos. 1, 2 and 3—demonstrated no pesticidal activity after 24 hours exposure.

TABLE 8

Compound names, numerical identifiers, and source for compounds.

| No. | Compound name | Source |
|---|---|---|
| 1 | 3-Carene* | Alaska yellow cedar, |
| 2 | Terpinen-4-ol* | Alaska yellow cedar, |
| 3 | Methyl carvacrol* | Alaska yellow cedar, |
| 4 | Carvacrol | Alaska yellow cedar, |
| 5 | Valencene | Alaska yellow cedar, |
| 6 | Nootkatene | Alaska yellow cedar, |
| 7 | Nootkatone, crystalline | Alaska yellow cedar, |
| 8 | Nootkatone | Grapefruit oil |
| 9 | Nootkatone | Synthetic |
| 10 | 13-hydroxy-valencene | Alaska yellow cedar, |
| 11 | Nootkatin | Alaska yellow cedar, |
| 12 | Nootkatol | Alaska yellow cedar, |
| 13 | Valencene-11,12-epoxide | Alaska yellow cedar, |
| 15 | Valencene-13-aldehyde | Valencene |
| 16 | Nootkatone-11,12-epoxide | Nootkatone |
| 17 | Nootkatone-1,10-epoxide | Nootkatone |
| 18 | Nootkatone-1,10-11,12-diepoxide | Nootkatone |

Tick colonies. Nymphal *I. scapularis* ticks (8-12 weeks old) were used in all trials and were obtained from the $F_1$ offspring of adult *I. scapularis* ticks collected in Bridgeport, Conn. There was no known pesticide used at this location. Ticks were maintained at 21° C., 90% RH, and received a 16:8 h (light:dark) cycle as described in Piesman, J., J. Med. Entomol. 30:199-203 (1993).

Flea Colonies. Adult *X. cheopis* fleas (1-3 wk old) were obtained from a colony founded more than eight years ago using adults received from Tom Schwan, Rocky Mountain Laboratories, Hamilton, Mont. The area from which these original adult fleas were obtained, and the resulting colony, have no known histories of pesticide exposure. Colonies were maintained in glass jars containing a 4:1:1:1 ratio of sawdust, dried beef blood, powedered milk, and powdered mouse chow and were held at 23° C., 85% RH, and received a 24 h dark cycle.

Mosquito Colonies. *Aedes aegypti* adult mosquitoes were obtained from an existing colony at the Centers for Disease Control and Prevention (CDC), Division of Vector-Borne Infectious Diseases (DVBID), Fort Collins, Colo. This colony has been maintained for over fifteen years with no known history of exposure to pesticides. Mosquitoes were reared at 28° C., 85% RH, and a 14:10 h (light:dark) cycle. Larvae were grown in de-ionized water and fed ground liver powder solution ad libitum. Fourth instars were removed and placed in emergence cages, and adults were fed a 2% sucrose solution until assayed. Adults were exposed to test products at 4-7 d after emergence.

Tick and Flea Bioassays. Concentrations of the compounds were prepared by 2-fold serial dilutions of a 0.5% (wt:vol) solution of the extracts in acetone. The approximate toxicity of individual compounds was determined with a total of 8 doses ranging from 0.002% to 0.25%. All 13 compounds were run in duplicate with more active compounds replicated once. A control treated with acetone only was run with each series. Tick and flea susceptibility was evaluated using a modified disposable pipette method. See, Barnard, D. R., et al., J. Econ. Entomol. 74:466-69 (1981).

Groups of 10 nymphal *I. scapularis* and *X. cheopis* fleas were used in all tests, resulting in a total of 5,240 nymphs and 4,860 fleas exposed to the compounds. The inner surface of 2-dram friction cap vials were treated with the compound/acetone solution, or acetone only as a control, and left to air-dry overnight. Three to 4 holes were made in the plastic cap to allow for air exchange. Nymphal ticks and adult fleas were then placed directly into the vials using forceps. Vials containing ticks or fleas were placed in desiccators for 24 h at 21° C. and 90% RH. Morbidity and mortality was recorded at 1, 2, 4, 8, and 24 h after initial exposure.

After 24 h, ticks were considered alive if they exhibited normal behavior when breathed upon or physically stimulated with wooden dowels. For each time point, if ticks were incapable of movement, maintaining normal posture, leg coordination, ability to right themselves, or any signs of life, they were considered moribund or dead. Results from tests where more than 10% of the control population died were discarded and retested.

Efficacies of individual compounds were determined by calculating lethal concentration 50% ($LC_{50}$) and 90% ($LC_{90}$) wt:vol by probit analysis using the LdP Line software (copyright 2000 by Ehab Mostafa Bakr), available via the Internet.

Mosquito Bioassay. Adult mosquitoes were tested using the bottle bioassay method of Brogden, W. G., and McAllister, J. C., J. Am. Mosq. Control Assoc. 14: 159-64 (1998), with minor modifications. Natural product extracts were two-fold serially diluted for a total of 8 concentrations ranging from 0.002% to 0.25% in 1.5 ml of acetone. Individual dilutions were added to 250 ml Wheaton glass bottles and capped. Bottles were manipulated to evenly coat all inner surfaces. The caps were removed and bottles were allowed to air-dry overnight. Once bottles were completely dry, 10-50 adult mosquitoes were aspirated into the bottles. Mosquitoes were held in the bottles for 24 h at 23° C. and 85% RH. Morbidity and mortality were recorded at 15, 30, 45, and 60 min and 24 hour intervals. One bottle for each replicate was treated with acetone only and served as a control. The dose-mortality data was evaluated with probit analysis, using the LdP Line software, to determine $LC_{50}$ and $LC_{90}$ values.

Residual Activity. To determine persistence of pesticidal activity of the compounds, 2-dram friction cap vials and 250 ml Wheaton glass bottles were treated using the same series of dilutions as described above. Treated vials and bottles, minus vector test species, were held at 21° C. with the ability of air exchange to take place (3-4 holes in the lids of 2-dram vials and lids on Wheaton bottles loosely applied). On day 7 after treatment, 2-dram vials were loaded with 10 ticks or 10 fleas and Wheaton bottles with 10-50 mosquitoes and held as previously described. Morbidity and mortality data for each test subject was recorded using the same time points. Any extracts that displayed acaricidal/insecticidal activity were retested at 2 and 4 wk after treatment. Dose mortality data was evaluated using probit analysis via the LdP Line software.

Results.

The susceptibility of *I. scapularis* nymphs, *X. cheopis* adults, and *Ae. aegypti* adults are presented in Tables 9-11 below. The terpenes, compounds 1-3, were found to be ineffective against all three arthropods in initial screenings, and, therefore were not further analyzed. The fourth terpene, carvacrol (compound 4), exhibited significant biological activity against ticks, fleas and mosquitoes with $LC_{50}$ values of 0.0068, 0.0059, and 0.0051 respectively.

Compounds 5-12 are eremophilane sesquiterpenes. Compound 5, valencene was effective only against mosquitoes and demonstrated an $LC_{50}$ of 0.015. Nootkatene, compound 6, was effective against all three pest species, demonstrating $LC_{50}$ values of 0.011 for ticks, 0.017 for fleas, and 0.027 for mosquitoes after 24 h. This compound did not demonstrate any residual activity after one week. The 3 preparations of nootkatone and β-hydroxy-valencene demonstrated the greatest activity in terms of $LC_{50}$ and $LC_{50}$ of the eremophilane sesquiterpenes. Compound 7, nootkatone from Alaska yellow cedar, was most effective against nymphal *I. scapularis*, with an observed $LC_{50}$ value of 0.0029. Adult *X. cheopis* were most susceptible to the natural grapefruit extract of nootkatone (compound 8) with an $LC_{50}$ value of 0.0029. Finally, compound 10 (13-hydroxy-valencene) proved to be the most toxic to adult mosquitoes ($LC_{50}$ of 0.0034).

Although there were slight differences in susceptibility to compounds 7-10, depending on the vector species, overall $LC_{50}$ and $LC_{90}$ values did not differ significantly. Of the last two compounds tested in the eremophilane sesquiterpene ring system (compounds 11 and 12), only compound 12 (nootkatol) exhibited biological activity against all three species. The $LC_{50}$ values were slightly greater for ticks ($LC_{50}$=0.023) and fleas ($LC_{50}$=0.024), but comparable to nootkatone against mosquitoes ($LC_{50}$=0.004).

The remaining five compounds (compounds 13 and 15-18) are derivatives of nootkatone and valencene. See Table 8. Compound 13, an epoxide, showed some activity against mosquitoes only ($LC_{50}$=0.295). Compounds 17 and 18 (nootkatone-1,10 epoxide and nootkatone diepoxide) had the greatest activity against fleas ($LC_{50}$=0.017 for compound 17 and $LC_{50}$=0.064 for compound 18) and ticks ($LC_{50}$=0.02 for compound 17 and $LC_{50}$=0.061 for compound 18). Valencene-13-aldehyde (compound 15) demonstrated $LC_{50}$ and $LC_{90}$ values equivalent to those of nootkatone and 13-hydroxy-valencene (compound 10): $LC_{50}$=0.0059 against ticks, $LC_{50}$=0.0049 against fleas and $LC_{50}$=0.0024 against mosquitoes.

Compounds were analyzed for residual activity based on results obtained for their 24 hour activities. A total of six compounds were examined with five demonstrating residual activity for at least four weeks, as shown in Tables 12-14. Compound 6 was nearly inactive beyond week after treatment and, therefore, not tested any further.

Compounds 7, 8, 9, 10 and 15 all demonstrated considerable biological activity through the four week time period. While the residual activity of compound 7 against *I. scapularis* nymphs remained virtually unchanged throughout the study, compounds 8 and 9 produced the lowest $LC_{50}$ values overall (Table 12). Compound 10 was still effective against ticks at four weeks, though a decrease in activity compared to earlier observations was noticed.

All five compounds remained active against fleas through the four-week period, with compound 7 producing the lowest $LC_{50}$ values (Table 13). Measurable residual activity was also observed in mosquitoes for all 5 compounds. Interestingly, the effectiveness of compounds 7 and 10 increased over the four week period (demonstrated by decreasing $LC_{50}$ values), while activity decreased for compounds 8 and 9 (Table 14). Compound 7 had the lowest $LC_{50}$ values after 4 wk against ticks ($LC_{50}$=0.026) and fleas ($LC_{50}$=0.031).

These dose-mortality results indicate that these compounds—such as nootkatone, carvacrol, 13-hydroxy-valencene, and valencene-13-aldehyde—function as effective pest control agents and pesticides. These compounds have the ability to knock down insects quickly and maintain a comparable level of activity for several weeks.

These individual compounds isolated from Alaska yellow cedar oil are more effective pest control agents than the crude oil itself, based on the $LC_{50}$ values observed for the crude oil against ticks ($LC_{50}$=0.151), mosquitoes ($LC_{50}$=0.032), and fleas ($LC_{50}$=0.337). These values are several times greater than what was observed for nootkatone, carvacrol, 13-hydroxy-valencene and valencene-13-aldehyde.

Furthermore, residual activity of the crude oil decreased rapidly after the initial treatment and was undetectable after 21 days against nymphal *I. scapularis*, indicating that the individual compounds obtained from the crude oil, and derivative compounds, are more stable and less volatile over time than the crude oil.

The methods used in these Examples are representative of types of applications occurring outside a laboratory setting. In most such applications, the pest would directly contact the compounds as they do in the bottles and vials, rather than ingesting the compound as a feed supplement, thus replicating conditions existing in a field setting. For example, the compound or composition might be applied to the walls of dwellings or stagnant pools of water to control mosquitoes, or it would be applied to vegetation or domesticated animals to control ticks and fleas.

TABLE 9

Response of *I. scapularis* nymphs after 24 h exposure.
(95% CI in parentheses; LC50 and LC90 values expressed in terms of percent concentration, wt:vol)

| Compound | $LC_{50}$ | $LC_{90}$ | Slope |
|---|---|---|---|
| 4 | 0.0068 (0.0054-0.0084) | 0.014 (0.011-0.022) | 3.906 |
| 5 | 0.598 | 44.837 | 0.684 |
| 6 | 0.011 (0.0086-0.014) | 0.06 (0.043-0.098) | 1.763 |
| 7 | 0.0029 (0.0025-0.0034) | 0.0055 (0.0046-0.0073) | 4.708 |
| 8 | 0.0061 (0.005-0.0072) | 0.015 (0.012-0.021) | 3.211 |
| 9 | 0.0033 (0.0027-0.004) | 0.0087 (0.0069-0.012) | 3.061 |
| 10 | 0.0051 (0.0041-0.0062) | 0.016 (0.013-0.023) | 2.562 |
| 11 | NE | NE | NE |
| 12 | 0.023 (0.017-0.03) | 0.059 (0.042-0.116) | 3.069 |
| 13 | 21.219 | 3713.114 | 0.571 |
| 15 | 0.0059 (0.0044-0.0076) | 0.017 (0.012-0.029) | 2.755 |
| 16 | NE | NE | NE |
| 17 | 0.02 (0.015-0.026) | 0.055 (0.04-0.092) | 2.883 |
| 18 | 0.061 (0.045-0.094) | 0.245 (0.142-0.756) | 2.131 |

NE = not effective at concentrations tested

TABLE 10

Response of *X. cheopis* adults after 24 h exposure.
(95% CI in parentheses; $LC_{50}$ and $LC_{90}$ values expressed in terms of percent concentration, wt:vol)

| Compound | $LC_{50}$ | $LC_{90}$ | Slope |
|---|---|---|---|
| 4 | 0.0059 (0.0047-0.0075) | 0.014 (0.011-0.023) | 3.413 |
| 5 | 0.041 (0.034-0.049) | 0.063 (0.052-0.093) | 6.925 |
| 6 | 0.017 (0.012-0.024) | 0.075 (0.049-0.151) | 2.022 |
| 7 | 0.0083 (0.0064-0.01) | 0.019 (0.015-0.031) | 3.527 |
| 8 | 0.0029 (0.002-0.0038) | 0.008 (0.0059-0.014) | 2.949 |
| 9 | 0.0066 (0.0046-0.0086) | 0.018 (0.013-0.032) | 2.9 |
| 10 | 0.0083 (0.0064-0.011) | 0.021 (0.016-0.035) | 3.143 |
| 11 | NE | NE | NE |
| 12 | 0.024 (0.018-0.034) | 0.1 (0.065-0.196) | 2.101 |
| 13 | NE | NE | NE |
| 15 | 0.0049 (0.0039-0.0058) | 0.0085 (0.0071-0.011) | 5.366 |
| 16 | NE | NE | NE |
| 17 | 0.017 (0.012-0.022) | 0.059 (0.041-0.108) | 2.326 |
| 18 | 0.064 (0.044-0.101) | 0.484 (0.284-1.609) | 1.455 |

NE = not effective at concentrations tested

TABLE 11

Response of *Ae. aegypti* after 24 h exposure.
(95% CI in parentheses; $LC_{50}$ and $LC_{90}$ values expressed in terms of percent concentration, wt:vol)

| Compound | $LC_{50}$ | $LC_{90}$ | Slope |
|---|---|---|---|
| 4 | 0.0051 | 0.014 | 2.908 |
| 5 | 0.015 (0.008-0.029) | 0.037 (0.031-0.162) | 3.199 |
| 6 | 0.027 | 0.059 | 3.696 |
| 7 | 0.0057 | 0.0092 | 6.22 |
| 8 | 0.0046 (0.004-0.0053) | 0.0087 (0.0072-0.011) | 4.635 |
| 9 | 0.0075 | 0.021 | 2.845 |
| 10 | 0.0034 (0.0024-0.0045) | 0.014 (0.01-0.023) | 2.094 |
| 11 | 0.852 | 7.869 | 1.327 |
| 12 | 0.004 (0.0032-0.0048) | 0.01 (0.008-0.014) | 3.201 |
| 13 | 0.295 (0.21-0.522) | 1.911 (0.922-7.257) | 1.581 |
| 15 | 0.0024 | 0.0034 | 8.714 |
| 16 | NE | NE | NE |
| 17 | 0.223 (0.158-0.402) | 2.001 (0.873-10.537) | 1.346 |
| 18 | 0.059 | 0.114 | 4.472 |

NE = not effective at concentrations tested

TABLE 12

Residual activivy against *Ixodes scapularis* nymphs at 1, 2, and 4 weeks.
(95% CI in parentheses; $LC_{50}$ and $LC_{90}$ values
expressed in terms of percent concentration, wt:vol)

| Compound | Weeks | $LC_{50}$ | $LC_{90}$ | Slope |
|---|---|---|---|---|
| 6 | 1 | 2.062 | 524.656 | 0.533 |
| 6 | 2 | NE | NE | NE |
| 6 | 4 | NE | NE | NE |
| 7 | 1 | 0.023 | 0.13 | 1.682 |
| 7 | 2 | 0.026 (0.018–0.039) | 0.168 (0.094–0.448) | 1.586 |
| 7 | 4 | 0.026 (0.018–0.039) | 0.164 (0.093–0.429) | 1.609 |
| 8 | 1 | 0.025 | 0.071 | 2.871 |
| 8 | 2 | 0.019 (0.014–0.024) | 0.056 (0.04–0.094) | 2.727 |
| 8 | 4 | 0.25 | 0.71 | 2.871 |
| 9 | 1 | 0.0084 (0.005–0.013) | 0.08 (0.045–0.22) | 1.304 |
| 9 | 2 | 0.0089 (0.0068–0.012) | 0.027 (0.02–0.045) | 2.649 |
| 10 | 1 | 0.0071 (0.0055–0.0091) | 0.019 (0.014–0.031) | 3.005 |
| 10 | 2 | 0.0083 (0.0057–0.011) | 0.044 (0.029–0.081) | 1.781 |
| 10 | 4 | 0.031 | 0.303 | 1.285 |
| 15 | 1 | 0.026 (0.02–0.033) | 0.072 (0.052–0.121) | 2.859 |

NE = not effective at concentrations tested

TABLE 13

Residual activivy against *Xenopsylla cheopis* adults nymphs
at 1, 2, and 4 weeks.
(95% CI in parentheses; $LC_{50}$ and $LC_{90}$ values
expressed in terms of percent concentration, wt:vol)

| Compound | Weeks | $LC_{50}$ | $LC_{90}$ | Slope |
|---|---|---|---|---|
| 6 | 1 | NE | NE | NE |
| 7 | 1 | 0.016 (0.012–0.02) | 0.05 (0.036–0.081) | 2.546 |
| 7 | 2 | 0.031 | 0.134 | 2.033 |
| 8 | 1 | 0.02 (0.016–0.026) | 0.053 (0.04–0.082) | 3.107 |
| 8 | 2 | 0.018 (0.013–0.024) | 0.081 (0.054–0.156) | 1.931 |
| 8 | 4 | 0.035 (0.026–0.051) | 0.161 (0.098–0.387) | 1.95 |
| 9 | 1 | 0.043 | 0.259 | 1.633 |
| 9 | 2 | 0.027 | 0.085 | 2.571 |
| 9 | 4 | 0.43 (0.034–0.056) | 0.111 (0.08–0.193) | 3.135 |
| 10 | 1 | 0.03 (0.022–0.041) | 0.113 (0.074–0.226) | 2.218 |
| 10 | 2 | 0.039 (0.029–0.053) | 0.131 (0.087–0.268) | 2.442 |
| 15 | 1 | 0.059 | 0.148 | 3.211 |

NE = not effective at concentrations tested

TABLE 14

Residual activivy against *Aedes aegypti* adults nymphs
at 1, 2, and 4 weeks.
(95% CI in parentheses; $LC_{50}$ and $LC_{90}$ values
expressed in terms of percent concentration, wt:vol)

| Compound | Weeks | $LC_{50}$ | $LC_{90}$ | Slope |
|---|---|---|---|---|
| 6 | 1 | 0.132 (0.096–0.236) | 0.659 (0.329–2.855) | 1.833 |
| 6 | 2 | NE | NE | NE |
| 6 | 4 | NE | NE | NE |
| 7 | 1 | 0.02 (0.014–0.029) | 0.054 (0.041–0.105) | 3.043 |
| 7 | 2 | 0.019 (0.016–0.022) | 0.046 (0.037–0.061) | 3.342 |
| 7 | 4 | 0.013 (0.011–0.015) | 0.038 (0.031–0.051) | 2.698 |
| 8 | 1 | 0.0065 | 0.014 | 3.858 |
| 8 | 2 | 0.0067 (0.0058–0.0076) | 0.012 (0.01–0.015) | 4.953 |
| 8 | 4 | 0.02 | 0.29 | 7.772 |
| 9 | 1 | 0.0089 (0.0077–0.01) | 0.018 (0.015–0.023) | 4.336 |
| 9 | 2 | 0.0042 (0.0036–0.0049) | 0.0088 (0.0074–0.011) | 4.014 |
| 9 | 4 | 0.018 | 0.036 | 4.169 |
| 10 | 1 | 0.024 (0.02–0.028) | 0.058 (0.046–0.081) | 3.286 |
| 10 | 2 | 0.014 (0.012–0.016) | 0.021 (0.019–0.027) | 6.932 |
| 10 | 4 | 0.013 (0.0089–0.017) | 0.04 (0.029–0.074) | 2.645 |
| 15 | 1 | 0.011 (0.0095–0.013) | 0.027 (0.022–0.037) | 3.392 |
| 15 | 2 | 0.014 (0.0074–0.025) | 0.037 (0.029–0.127) | 3.136 |

NE = not effective at concentrations tested

Example 10

Pesticidally Acceptable Compositions

Compositions suitable for pesticidal uses are described, including solid, liquid, and gaseous formulations.

Dusts

|  | Component | Amount (by weight) |
|---|---|---|
| Dust A | 13-hydroxy-valencene | 2% |
|  | highly dispersed silica | 1% |
|  | talcum | 97% |
| Dust B | valencene-11,12-epoxide | 1% |
|  | highly dispersed silica | 5% |
|  | talcum | 94% |
| Dust C | valencene-13-aldehyde | 1% |
|  | valencene-11,12-epoxide | 1% |
|  | sodium sulfate | 98% |

Ready-to-use dusts may be obtained by intimately mixing the carriers with the active ingredients.

Emulsifiable Concentrate

| Component | Amount (by weight) |
|---|---|
| nootkatone-1,10-epoxide | 2% |
| octylphenol polyethoxylate | 3% |
| calcium dodecylbenzenesulfonate | 3% |
| polyethoxylated castor oil | 2% |
| cyclohexanone | 35% |
| xylene mixture | 55% |

An emulsions of a desired concentration may be prepared from this concentrate by dilution with water.

Extruder Granules

| Component | Amount (by weight) |
|---|---|
| 13-hydroxy-valencene | 10% |
| sodium ligninsulfonate | 2% |
| carboxymethyl cellulose | 1% |
| kaolin | 87% |

The active ingredient is mixed with the additives, the mixture is ground together, water is added to the mixture, and the mixture is then extruded, granulated, and subsequently dried.

Example 11

Production of Compound 15 (Valencene-13-aldehyde)

Valencene-13-aldehyde was produced by the reaction:

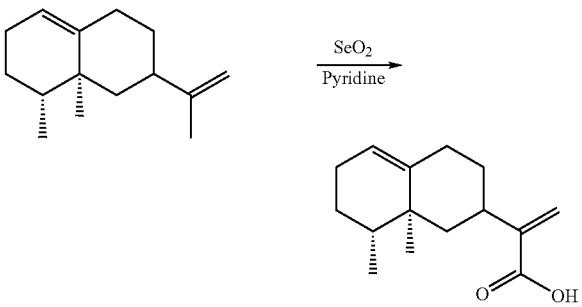

using the following procedure: one gram (4.89 mmol) of valencene was dissolved in 10 ml of dry pyridine. The solution was stirred and 1 g (9.01 mmol) of $SeO_2$ was added to the reaction. The mixture was refluxed for 5 hours until the yellow solution turned black. The mixture was filtered to eliminate the selenium dust. The brown solution was passed through Silica gel-$Na_2CO_3$ 1:1 and the funnel was washed with ether. The pyridine was removed by vacuum distilation and the remaining oil was analyzed by chromatography through Silica gel-$Na_2CO_3$ 1:1 with hexane as eluent recovering the most polar fraction (Rf =0.2 in hexane). After solvent evaporation, a yellow oil (0.125 g, 11.59% yield) was obtained, showing just one product in high purity.

Example 12

Production of Compound 16 (Nootkatone-11,12-epoxide)

Nootkatone-11,12-epoxide was produced by the reaction:

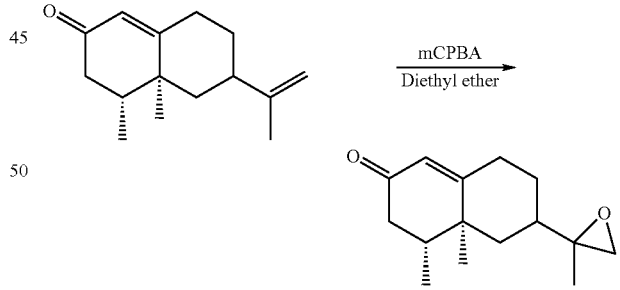

using the following procedure: four grams of nootkatone (18.32 mmol) were dissolved in 30 ml of diethyl ether and 3.79 g (18.32 mmol) of m-chloroperbenzoic acid (mCPBA 80%) were added while stirring. After two hours, an excess of one mol (3.79 g) of mCPBA 80% was added. The solution was stirred for two hours more, then 30 ml of cold water and 30 ml of $NaHCO_3$ saturated solution was added to stop the reaction. The mixture was poured through a separatory funnel to separate the organic layer. The remaining water layer was washed twice with diethyl ether (30 ml) and joined with the first one. The organic layer containing diethyl ether and the product was dried with anhydrous sodium sulfate, and ether was removed with rotavap or by nitrogen flow yielding 2.5 g (58% yield) of product as a coalescent pale yellow oil that eventually crystallized (rf=0.24 in hexane-diethyl ether 1:1).

The principle epoxide product showed a high purity by NMR analysis (>90%). However, some efforts to purify the compound by silica gel-sodium carbonate chromatography yielded a mixture of open products, likely diols. Some crystals of the pure product were obtained by passing a small quantity of the crude epoxide through a Na$_2$CO$_3$-silica gel (7:3) column yielding white crystals that melted at 35.2-35.7° C.

Example 13

Production of Compound 17
(Nootkatone-1,10-epoxide)

Nootkatone-1,10-epoxide was produced by the reaction:

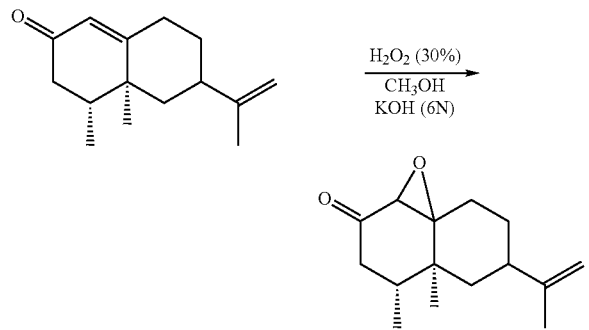

using the following procedure: five grams (22.29 mmol) of nootkatone were dissolved in 30 ml of methanol, the solution was cooled to 10° C. while stirring, then 4.67 g (133.74 mmol, 15.56 ml) of H$_2$O$_2$ (30%) was added. When the addition was finished, 10 ml of KOH 6N was added drop by drop over a period of 20 minutes, taking care that the temperature did not exceed 10° C. After the KOH addition, the mixture was stirred for 3 hours at 25° C., the methanol was evaporated in a rotavap, and the product was extracted from the water solution by diethyl ether (3×20 ml). The organic solution with the product was dried on anhydrous Na$_2$SO$_4$ and the ether completely eliminated by evaporation to give 2.97 g (44.4% yield) of a colorless oil (rf=0.44 in Hexane-Acetone 9:1), NMR analysis of the product showed high purity.

Example 14

Production of Compound 18
(Nootkatone-1,10-11,12-diepoxide)

Nootkatone-1,10-11,12-diepoxide was produced by the reaction:

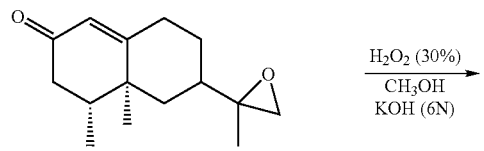

-continued

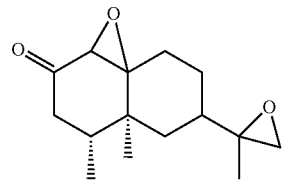

using the following procedure: 1.7 g (7.26 mmol) of the epoxide were dissolved in 50 ml of anhydrous methanol, the solution was cooled to 10° C., then 2.5 ml (0.75 g, 22.06 mmol) was added drop by drop while stirring, over a period of 20 minutes, taking care that the temperature did exceed 10° C. After the KOH addition, the mixture was stirred for 3 hours then killed with 30 ml of cold water. The methanol was eliminated in a rotavap and the water solution was extracted with diethyl ether (3×20 ml). The ethereal solution containing the product was evaporated by rotavap or by nitrogen flow, yielding 0.735 g (40.5%) of the diepoxide as a semisolid white, (rf=0.50 in hexane-acetone 1:1). $^{13}$C-NMR showed a mixture of diastereo isomers with high purity.

Having illustrated and described the principles of the invention by several embodiments, it should be apparent that those embodiments can be modified in arrangement and detail without departing from the principles of the invention. Thus, the invention as claimed includes all such embodiments and variations thereof, and their equivalence, as come within the true spirit and scope of the claims stated below.

The invention claimed is:

1. A method for controlling an arthropod, comprising contacting an arthropod selected from the taxonomic order or subclass Acarina, Anoplura, Blattaria, Homoptera, Hymenoptera, Lepidoptera, or Siphonaptera, with a pesticidally effective amount of a pest control agent comprising isolated nootkatone, wherein the nootkatone is present in a concentration of at least about 0.01 ppm (parts per million) and less than 65×10$^{-3}$ percent (wt:vol), and a pesticidally acceptable carrier.

2. The method of claim 1, wherein controlling the arthropod comprises killing the arthropod.

3. The method of claim 1, wherein controlling the arthropod comprises repelling the arthropod.

4. The method of claim 1, wherein the pest control agent is applied directly to the arthropod.

5. The method of claim 1, wherein the pest control agent is applied to a locus comprising the arthropod.

6. The method of claim 1, wherein the method comprises an area-wide application of the pest control agent.

7. The method of claim 1, wherein the pest control agent is provided to a human or non-human animal.

8. The method of claim 7, wherein the pest control agent is orally administered or provided as a topical treatment.

9. The method of claim 1, wherein the pest control agent is embedded within a material.

10. The method of claim 9, wherein the material is a collar, ear tag, piece of clothing, siding, wall studs, or beam.

11. The method of claim 1, wherein the pest control agent is applied to plants, animals or objects within an environment that comes into contact with the arthropod.

12. The method of claim 1, wherein the arthropod is a member of the taxonomic order Siphonaptera.

13. The method of claim 12, wherein the arthropod is *Xenopsylla cheopis* (rat flea).

14. The method of claim 1, wherein the arthropod is a member of the *Ixodes* species.

15. The method of claim 14, wherein the arthropod is *Ixodes scapularis* (deer tick).

16. The method of claim 1, further comprising identifying the arthropod as a vector for a disease.

17. The method of claim 16, wherein the disease is Lyme disease; tick borne-babesiosis; tularemia; powassan-like virus infection; tick borne encephalitis; relapsing fever; Colorado Tick Fever; ehrlichiosis; Rocky Mountain Spotted Fever; or the Plague.

18. The method of claim 1, wherein the isolated nootkatone is present in a concentration of at least about 0.1 ppm (parts per million).

19. The method of claim 1, wherein the nootkatone comprises synthetic nootkatone.

20. The method of claim 1, wherein the nootkatone is isolated from Alaska yellow cedar.

21. A method for controlling an arthropod, comprising contacting an arthropod selected from the taxonomic order or subclass Acarina, Anoplura, Blattaria, Homoptera, Hymenoptera, Lepidoptera, or Siphonaptera with a pesticidally effective amount of a pesticidal composition consisting essentially of nootkatone and a pesticidally acceptable carrier, wherein the nootkatone is present in a concentration of at least about 0.01 ppm (parts per million) and less than $65 \times 10^{-3}$ percent (wt:vol).

22. The method of claim 21, wherein controlling the arthropod comprises killing the arthropod.

23. The method of claim 21, wherein controlling the arthropod comprises repelling the arthropod.

24. A method for controlling an arthropod, comprising contacting an arthropod selected from the taxonomic order or subclass Acarina, Anoplura, Blattaria, Homoptera, Hymenoptera, Lepidoptera, or Siphonaptera with a pesticidally effective amount of a pesticidal composition comprising a pesticidal eremophilane sesquiterpene and a pesticidally acceptable carrier; wherein the pesticidal eremophilane sesquiterpene consists of nootkatone, and wherein the nootkatone is present in a concentration of at least about 0.01 ppm (parts per million) and less than $65 \times 10^{-3}$ percent (wt:vol).

25. The method of claim 1, wherein the arthropod is a member of the taxonomic order Anoplura.

26. The method of claim 25, wherein the arthropod is a member of the *Pediculus* species.

27. The method of claim 21, wherein the isolated nootkatone is present in a concentration of at least about 0.1 ppm (parts per million).

* * * * *

UNITED STATES PATENT AND TRADEMARK OFFICE
CERTIFICATE OF CORRECTION

| | |
|---|---|
| PATENT NO. | : 7,629,387 B2 |
| APPLICATION NO. | : 11/105807 |
| DATED | : December 8, 2009 |
| INVENTOR(S) | : Maupin et al. |

It is certified that error appears in the above-identified patent and that said Letters Patent is hereby corrected as shown below:

Column 10, line 53, "$C_1$-$R_2$" should read -- $C_{11}$-$R_2$ --

Column 33, line 62, "$R_f$ 0.43" should read -- Rf 0.43 --

Column 34, line 15, "$R_f$ 0.36" should read -- Rf 0.36 --

Column 40, line 25, "β-hydroxy-valencene" should read -- 13-hydroxy-valencene --

Signed and Sealed this

Twelfth Day of October, 2010

David J. Kappos
*Director of the United States Patent and Trademark Office*